(12) United States Patent
Crespo Crespo et al.

(10) Patent No.: US 7,354,936 B2
(45) Date of Patent: *Apr. 8, 2008

(54) 2-PHENYLPYRAN-4-ONE DERIVATIVES

(75) Inventors: Maria Isabel Crespo Crespo, Barcelona (ES); Juan Miguel Jimenez Mayorga, Barcelona (ES); Josep Lluis Matallana Julia, Barcelona (ES); Joan Feixas Gras, Barcelona (ES)

(73) Assignee: Almirall AG, Baar (CH)

( * ) Notice: Subject to any disclaimer, the term of this patent is extended or adjusted under 35 U.S.C. 154(b) by 648 days.

This patent is subject to a terminal disclaimer.

(21) Appl. No.: 10/245,873

(22) Filed: Sep. 16, 2002

(65) Prior Publication Data

US 2003/0232880 A1    Dec. 18, 2003

Related U.S. Application Data

(63) Continuation of application No. PCT/EP01/03042, filed on Mar. 16, 2001.

(30) Foreign Application Priority Data

Mar. 16, 2000   (ES)   ............... 200000637

(51) Int. Cl.
*A01N 43/64* (2006.01)
*A01N 43/06* (2006.01)
*C07D 311/00* (2006.01)
*C07D 307/00* (2006.01)
*C07D 307/87* (2006.01)

(52) U.S. Cl. ............... 514/336; 514/444; 514/459; 514/462; 546/282.1; 549/66; 549/413; 549/419; 549/423

(58) Field of Classification Search ............... 549/417, 549/419, 423, 60; 546/282.1; 514/336, 514/444, 459, 460
See application file for complete search history.

(56) References Cited

U.S. PATENT DOCUMENTS

| | | | |
|---|---|---|---|
| 3,784,691 A | 1/1974 | Fitzi et al. | |
| 3,901,908 A | 8/1975 | Fitzi et al. | |
| 4,304,728 A | 12/1981 | Clark et al. | |
| 6,048,850 A | 4/2000 | Young et al. | |
| 6,348,468 B1 | 2/2002 | Ohkushi et al. | |
| 6,518,303 B2 * | 2/2003 | Crespo Crespo et al. | ... 514/459 |

FOREIGN PATENT DOCUMENTS

| | | |
|---|---|---|
| DE | 2064520 | 7/1971 |
| EP | 0 714 883 | 6/1996 |
| EP | 1 043 317 | 10/2000 |
| GB | 1 328 550 | 8/1973 |
| GB | 2 047 697 | 12/1980 |
| WO | WO 95/14014 | 5/1995 |
| WO | WO 96/06840 | 3/1996 |
| WO | WO 96/31509 | 10/1996 |
| WO | WO 99/25697 | 5/1999 |
| WO | WO 00/18753 | 4/2000 |
| WO | WO 00/18753 A1 * | 4/2000 ................. 514/459 |

OTHER PUBLICATIONS

Shiel MD, COX-2 Inhibitors Dilema medicinenet.com (2005).*
Dr. Gotlieb COX 1 dn 2 cyclo-oxygenase systems (1999).*
Fujiwara, Risa al., (1992). "Sensitizer for Thermal Recording and Thermal Recording Material," *Chemical Abstracts*, Columbus, Ohio, 117(74):719, abstract No. 117:202023e.
Protiva, Miroslav et al., (1976). "Parasympatholytic Piperazine Derivatives," *Chemical Abstracts*, Columbus, Ohio, 84(9):538, abstract No. 84:59566b.
Saettone, M. F. (Jun. 1966). "Reactions of 3,4-Disubstituted 4-Oxazolin-2-ones. I. A Novel Route to 1,3,5-Trisubstituted Hydantoins," *J. Org. Chem.* 31:1959-1963.
Valenta, V. et al., (1983) "α-(4-tolyl)dopamine, derivatives and analogues; synthesis and pharmacological screening," *Collection Czechoslovak Chem. Commun.* 48:1447-1463.

* cited by examiner

*Primary Examiner*—Janet L. Andres
*Assistant Examiner*—Raymond Covington
(74) *Attorney, Agent, or Firm*—Morrison & Foerster LLP

(57) ABSTRACT

The present invention relates to 2-(4-sulphonylphenyl)pyran-4-one derivatives of general formula

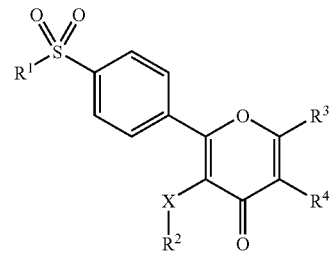

processes for their preparation, pharmaceutical compositions containing them, and their medical uses.

21 Claims, No Drawings

2-PHENYLPYRAN-4-ONE DERIVATIVES

CROSS REFERENCE TO RELATED APPLICATIONS

This application is a continuation of International Application No. PCT/EP01/03042 filed Mar. 16, 2001 and published in English on Sep. 20, 2001, which claims the benefit of Spainish Application No. 200000637, filed Mar. 16, 2000, the contents of which are incorporated herein by reference.

This invention relates to new therapeutically useful 2-phenylpyran-4-one derivatives, to processes for their preparation and to pharmaceutical compositions containing them.

It is known that non-selective inhibition of the enzyme cyclooxygenase (COX) prevents the overproduction of prostaglandins associated with inflammation, which are mediated by cyclooxygenase-2 (COX-2) but, at the same time, deprives tissues of basal levels of prostaglandins necessary for the health of certain tissues mediated largely by cyclooxygenase-1 (COX-1). Non steroidal anti-inflammatory drugs are non-selective inhibitors of COX and for that reason, have side effects of decreased renal blood flow, decreased platelet function, dyspepsia and gastric ulceration.

We have now found that certain 2-phenylpyran-4-one derivatives selectively inhibit COX-2 in preference to COX-1 and are useful in the treatment of COX-2 mediated diseases, such as inflammation, pain, fever, and asthma with fewer side effects.

Accordingly the present invention provides a 2-phenylpyran-4-one compound of formula (I):

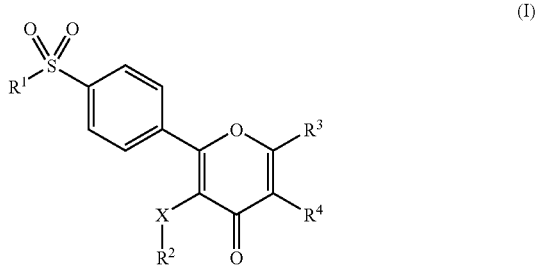

wherein:

$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkyl, hydroxymethyl, alkoxymethyl, alkenyloxymethyl, $C_3$-$C_7$ cycloalkoxymethyl, $C_3$-$C_7$ cycloalkylmethoxymethyl, benzyloxymethyl, hydroxycarbonyl, nitrile, trifluoromethyl or difluoromethyl group or a $R^7$—COO—$CH_2$— group wherein $R^7$ represents an alkyl or phenyl group;

$R^4$ represents a hydrogen atom, or an alkyl, alkenyl or alkynyl group or a halogen atom; and X represents a single bond, an oxygen atom, a sulfur atom or a methylene group;

or a pharmaceutically acceptable salt thereof.

In the compounds of formula (I), when $R^3$ is an alkenyloxymethyl group, it is typically an alkenylmethoxymethyl group.

In a preferred embodiment the invention provides a compound of formula (I):

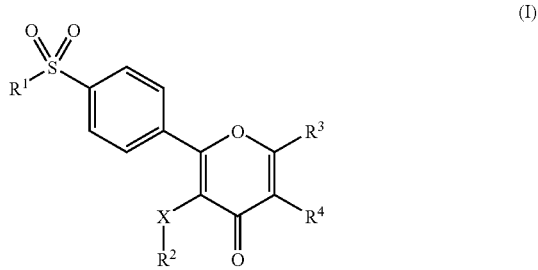

wherein:

$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkyl, hydroxymethyl, alkoxymethyl, alkenyloxymethyl, $C_3$-$C_7$ cycloalkoxymethyl, $C_3$-$C_7$ cycloalkylmethoxymethyl, benzyloxymethyl, hydroxycarbonyl, nitrile, trifluoromethyl or difluoromethyl group or a $R^7$—COO—$CH_2$— group wherein $R^7$ represents an alkyl or phenyl group;

$R^4$ represents a hydrogen atom, or an alkyl, alkenyl or alkynyl group or a halogen atom; and X represents a single bond, an oxygen atom, a sulfur atom or a methylene group; with the proviso that when $R^4$ is a hydrogen atom $R^3$ is an alkenylmethoxymethyl, $C_3$-$C_7$ cycloalkylmethoxymethyl or $R^7$—COO—$CH_2$— group wherein $R^7$ represents an alkyl or phenyl group;

or a pharmaceutically acceptable salt thereof.

In this preferred embodiment, when $R^3$ is an alkenyloxymethyl group, it is typically an alkenylmethoxymethyl group.

In another preferred embodiment the invention provides a compound of formula (I):

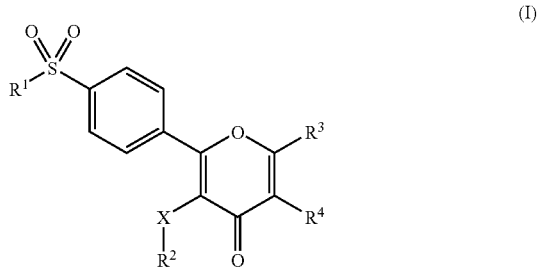

wherein:

$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkyl, hydroxymethyl, alkoxymethyl, alkenyloxymethyl, $C_3$-$C_7$ cycloalkoxymethyl, $C_3$-$C_7$ cycloalkylmethoxymethyl, benzyloxymethyl, hydroxycarbonyl, nitrile, trifluoromethyl or difluoromethyl group or a $R^7$—COO—$CH_2$— group wherein $R^7$ represents an alkyl or phenyl group;

$R^4$ represents an alkyl, alkenyl or alkynyl group or a halogen atom; and

X represents a single bond, an oxygen atom, a sulfur atom or a methylene group;

or a pharmaceutically acceptable salt thereof.

In this further preferred embodiment, when $R^3$ is an alkenyloxymethyl group, it is typically an alkenylmethoxymethyl group.

In another preferred embodiment the invention provides a compound of formula (I):

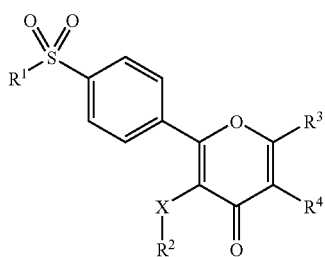

(I)

wherein:

$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkenyloxymethyl or $C_3$-$C_7$ cycloalkylmethoxymethyl group or a $R^7$—COO—$CH_2$— group wherein $R^7$ represents an alkyl or phenyl group;

$R^4$ represents a hydrogen atom; and

X represents a single bond, an oxygen atom, a sulfur atom or a methylene group;

or a pharmaceutically acceptable salt thereof.

In this further preferred embodiment, when $R^3$ is an alkenyloxymethyl group, it is typically an alkenylmethoxymethyl group.

In another preferred embodiment the invention provides a compound of formula (IA):

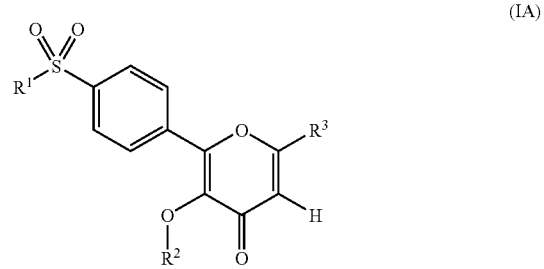

(IA)

wherein:

$R^1$ represents a methyl or ethyl group;

$R^2$ represents a phenyl group which may be unsubstituted or substituted by one or more substituents selected from halogen atoms or alkyl, trifluoromethyl, hydroxy, alkoxy, methylthio, amino, mono- or dialkylamino, hydroxyalkyl or hydroxycarbonyl groups;

$R^3$ represents an alkyl, hydroxymethyl, alkoxymethyl, $C_3$-$C_7$ cycloalkoxymethyl, benzyloxymethyl, hydroxycarbonyl, nitrile, trifluoromethyl or difluoromethyl group;

provided that when $R^3$ is methyl, $R^2$ is either (a) a phenyl group having at least one substituent selected from trifluoromethyl, hydroxy, alkoxy, methylthio, amino, mono- or dialkylamino, hydroxyalkyl or hydroxycarbonyl groups, (b) a monosubstituted phenyl group having a halogen atom or an alkyl group at the 3-position or having a bromine atom or an alkyl group at the 2-position 1 or (c) a phenyl group having two or more substituents wherein at least one substituent is a bromine atom or wherein an alkyl group is present at the 2- or 4-position, or (d) 3-methyl-4-fluorophenyl;

or a pharmaceutically acceptable salt thereof.

In the compounds of formula (IA), $R^1$ is typically a methyl group. Further, when $R^3$ is a methyl group, $R^2$ is typically phenyl having at least one substituent selected from trifluoromethyl, hydroxy, alkoxy, methylthio, amino, mono- or dialkylamino, hydroxyalkyl or hydroxycarbonyl groups; with the substituent preferably being selected from hydroxy, alkoxy, methylthio, amino, mono- or dialkylamino, hydroxyalkyl or hydroxycarbonyl groups.

The invention also provides a compound of formula (IB):

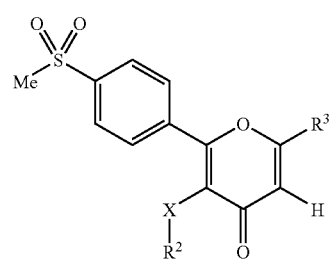

(IB)

wherein:

$R^2$ represents a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

R³ represents an alkyl, hydroxymethyl, alkoxymethyl, $C_3$-$C_7$ cycloalkoxymethyl, benzyloxymethyl, hydroxycarbonyl, nitrile, trifluoromethyl or difluoromethyl group;

or a pharmaceutically acceptable salt thereof.

In the formulae (IA) and (IB), R³ is typically a hydroxymethyl, methoxymethyl, ethoxymethyl, propoxymethyl, isopropoxymethyl, difluoromethyl, hydroxycarbonyl, cyclopropoxymethyl or cyclobutoxymethyl group.

The alkyl groups and moieties such as those present in the alkoxy, hydroxyalkyl, mono- or di-alkylamino groups, mentioned in relation to the groups R¹ to R⁷ are usually "lower" alkyl that is containing from 1 to 6 particularly from 1 to 4 carbon atoms, the hydrocarbon chain being branched or straight. Preferred alkyl groups, and where relevant alkyl moieties, include methyl, ethyl, propyl including i-propyl, and butyl including n-butyl, t-butyl and sec-butyl.

In a phenyl group substituted by one or more halogen atoms or alkyl, trifluoroalkyl, hydroxy, alkoxy, methylthio, amino, mono- or dialkyl amino, hydroxyalkyl or hydroxycarbonyl groups, the phenyl ring may be substituted by 1, 2, 3, 4 or 5 substituents, preferably 1, 2 or 3 substituents, each being independently selected from the possible substituents set out above. That is to say, the phenyl group (attached to X or the pyran-4-one ring through its 1-position) may be substituted at any of the remaining positions, that is to say the 2, 3, 4, 5 or 6-positions. A phenyl group having more than one substituent may be substituted at any combination of positions. For example a phenyl group having two substituents may be substituted at the 2 and 3, 2 and 4, 2 and 5, 2 and 6, 3 and 4 or 3 and 5 positions.

In particular, it is preferred that R² represents a branched alkyl, $C_3$-$C_7$ (preferably $C_3$, $C_5$ or $C_6$) cycloalkyl, napthyl, tetrahydronaphthyl or indanyl group, an unsubstituted phenyl group or a phenyl group substituted by one or more halogen atoms, alkyl groups, preferably methyl groups, and/or alkoxy groups, preferably methoxy groups. Halogen atoms are preferably selected from fluorine, chlorine or bromine atoms.

R² is preferably a phenyl group that is unsubstituted or has 1, 2 or 3 substituents, more preferably 1 or 2 substituents. Preferably the substituents are independently selected from methyl groups and chlorine, bromine and fluorine atoms. When R² is a phenyl group substituted by one or more halogens atoms and/or alkyl groups, preferably one of the substitutions is at the 2- or 3-position of the phenyl group.

In one preferred group of compounds R² is an unsubstituted phenyl group or a phenyl group substituted by a single halogen atom selected from fluorine, chlorine or bromine, a single methyl group or two halogen atoms which are the same or different and are selected from fluorine, chlorine or bromine.

It is preferred that R¹ independently represents an unsubstituted alkyl group such as methyl, ethyl, propyl or butyl, preferably methyl or an $NH_2$ group (i.e. R⁵ and R⁶ in the above formula both independently represent an H atom).

It is also preferred that R³ independently represents an unsubstituted $C_{1-3}$ alkyl group such as methyl, ethyl or n-propyl or i-propyl, a nitrile group, a hydroxymethyl group, a methoxymethyl group, an ethoxymethyl group, a propoxymethyl group, an isopropoxymethyl group, a difluoromethyl group, a propenyloxymethyl group, a hydroxycarbonyl group, a cyclopropoxymethyl group, a cyclobutoxymethyl group, a cyclopropylmethoxymethyl group, a cyclobutylmethyloxymethyl group or a $CH_3$—COO—$CH_2$— group.

It is preferred that R⁴ represents an alkyl group such as methyl or ethyl, an alkenyl group such as vinyl, an alkynyl group such as ethynyl, a halogen atom such as a chlorine or bromine atom or a hydrogen atom.

It is preferred that X independently represents a single bond, an oxygen atom or a methylene group more preferably a single bond or an oxygen atom and most preferably an oxygen atom.

Specific examples of the 2-phenylpyran-4-one derivatives of the present invention include:

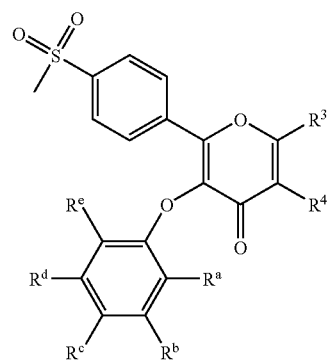

| R³ | R⁴ | Rᵃ | Rᵇ | Rᶜ | Rᵈ | Rᵉ |
|----|----|----|----|----|----|----|
| Me | H  | H  | Br | H  | H  | H  |
| Me | H  | Br | H  | H  | H  | H  |
| Me | H  | H  | Me | H  | H  | H  |
| Me | H  | Me | H  | H  | H  | H  |
| Me | H  | Me | H  | F  | H  | H  |
| Me | H  | Me | H  | Cl | H  | H  |
| Me | H  | F  | H  | Me | H  | H  |
| Me | H  | Cl | H  | Me | H  | H  |
| Me | H  | H  | Me | F  | H  | H  |
| Me | H  | H  | F  | Me | H  | H  |
| Me | H  | H  | Cl | Me | H  | H  |
| Me | H  | F  | H  | Br | H  | H  |
| Me | H  | Cl | H  | Br | H  | H  |
| Me | H  | Br | H  | Br | H  | H  |
| Me | Cl | H  | H  | H  | H  | H  |
| Me | Cl | H  | H  | F  | H  | H  |
| Me | Cl | H  | F  | H  | H  | H  |
| Me | Cl | F  | H  | H  | H  | H  |
| Me | Cl | H  | H  | Cl | H  | H  |
| Me | Cl | H  | Cl | H  | H  | H  |
| Me | Cl | Cl | H  | H  | H  | H  |
| Me | Cl | H  | H  | Br | H  | H  |
| Me | Cl | H  | Br | H  | H  | H  |
| Me | Cl | Br | H  | H  | H  | H  |
| Me | Cl | H  | H  | Me | H  | H  |
| Me | Cl | H  | Me | H  | H  | H  |
| Me | Cl | Me | H  | H  | H  | H  |
| Me | Cl | F  | H  | F  | H  | H  |
| Me | Cl | F  | H  | H  | F  | H  |
| Me | Cl | H  | F  | F  | H  | H  |
| Me | Cl | F  | H  | H  | H  | F  |
| Me | Cl | Cl | H  | Cl | H  | H  |
| Me | Cl | Cl | H  | H  | Cl | H  |
| Me | Cl | H  | Cl | Cl | H  | H  |
| Me | Cl | Cl | H  | H  | H  | Cl |
| Me | Cl | F  | H  | Cl | H  | H  |
| Me | Cl | Cl | H  | F  | H  | H  |
| Me | Cl | F  | H  | Br | H  | H  |
| Me | Cl | Br | H  | F  | H  | H  |
| Me | Cl | H  | Cl | F  | H  | H  |
| Me | Cl | H  | F  | Cl | H  | H  |
| Me | Cl | F  | H  | Me | H  | H  |
| Me | Cl | Cl | H  | Me | H  | H  |
| Me | Cl | Me | H  | F  | H  | H  |
| Me | Cl | Me | H  | Cl | H  | H  |
| Me | Cl | H  | Me | F  | H  | H  |

-continued

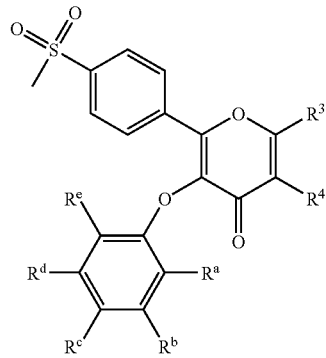

| R³ | R⁴ | Rᵃ | Rᵇ | Rᶜ | Rᵈ | Rᵉ |
|---|---|---|---|---|---|---|
| Me | Cl | H | Me | Cl | H | H |
| Me | Cl | H | F | Me | H | H |
| Me | Cl | H | Cl | Me | H | H |
| Me | Br | H | H | H | H | H |
| Me | Br | H | H | F | H | H |
| Me | Br | H | F | H | H | H |
| Me | Br | F | H | H | H | H |
| Me | Br | H | H | Cl | H | H |
| Me | Br | H | Cl | H | H | H |
| Me | Br | Cl | H | H | H | H |
| Me | Br | H | H | Br | H | H |
| Me | Br | H | Br | H | H | H |
| Me | Br | Br | H | H | H | H |
| Me | Br | H | H | Me | H | H |
| Me | Br | H | Me | H | H | H |
| Me | Br | Me | H | H | H | H |
| Me | Br | F | H | F | H | H |
| Me | Br | F | H | H | F | H |
| Me | Br | H | F | F | H | H |
| Me | Br | F | H | H | H | F |
| Me | Br | Cl | H | Cl | H | H |
| Me | Br | Cl | H | H | Cl | H |
| Me | Br | H | Cl | Cl | H | H |
| Me | Br | Cl | H | H | H | Cl |
| Me | Br | F | H | Cl | H | H |
| Me | Br | Cl | H | F | H | H |
| Me | Br | F | H | Br | H | H |
| Me | Br | Br | H | F | H | H |
| Me | Br | H | Cl | F | H | H |
| Me | Br | H | F | Cl | H | H |
| Me | Br | F | H | Me | H | H |
| Me | Br | Cl | H | Me | H | H |
| Me | Br | Me | H | F | H | H |
| Me | Br | Me | H | Cl | H | H |
| Me | Br | H | Me | F | H | H |
| Me | Br | H | Me | Cl | H | H |
| Me | Br | H | F | Me | H | H |
| Me | Br | H | Cl | Me | H | H |
| Me | Me | H | H | H | H | H |
| Me | Me | H | H | F | H | H |
| Me | Me | H | F | H | H | H |
| Me | Me | F | H | H | H | H |
| Me | Me | H | H | Cl | H | H |
| Me | Me | H | Cl | H | H | H |
| Me | Me | Cl | H | H | H | H |
| Me | Me | H | H | Br | H | H |
| Me | Me | H | Br | H | H | H |
| Me | Me | Br | H | H | H | H |
| Me | Me | H | H | Me | H | H |
| Me | Me | H | Me | H | H | H |
| Me | Me | Me | H | H | H | H |
| Me | Me | F | H | F | H | H |
| Me | Me | F | H | H | F | H |
| Me | Me | H | F | F | H | H |
| Me | Me | F | H | H | H | F |
| Me | Me | Cl | H | Cl | H | H |
| Me | Me | Cl | H | H | Cl | H |
| Me | Me | H | Cl | Cl | H | H |
| Me | Me | Cl | H | H | H | Cl |

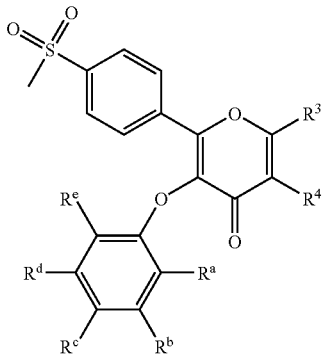

| R³ | R⁴ | Rᵃ | Rᵇ | Rᶜ | Rᵈ | Rᵉ |
|---|---|---|---|---|---|---|
| Me | Me | F | H | Cl | H | H |
| Me | Me | Cl | H | F | H | H |
| Me | Me | F | H | Br | H | H |
| Me | Me | Br | H | F | H | H |
| Me | Me | H | Cl | F | H | H |
| Me | Me | H | F | Cl | H | H |
| Me | Me | F | H | Me | H | H |
| Me | Me | Cl | H | Me | H | H |
| Me | Me | Me | H | F | H | H |
| Me | Me | Me | H | Cl | H | H |
| Me | Me | H | Me | F | H | H |
| Me | Me | H | Me | Cl | H | H |
| Me | Me | H | F | Me | H | H |
| Me | Me | H | Cl | Me | H | H |
| Me | CH=CH₂ | H | H | H | H | H |
| Me | CH=CH₂ | H | H | F | H | H |
| Me | CH=CH₂ | H | F | H | H | H |
| Me | CH=CH₂ | F | H | H | H | H |
| Me | CH=CH₂ | H | H | Cl | H | H |
| Me | CH=CH₂ | H | Cl | H | H | H |
| Me | CH=CH₂ | Cl | H | H | H | H |
| Me | CH=CH₂ | H | H | Br | H | H |
| Me | CH=CH₂ | H | Br | H | H | H |
| Me | CH=CH₂ | Br | H | H | H | H |
| Me | CH=CH₂ | H | H | Me | H | H |
| Me | CH=CH₂ | H | Me | H | H | H |
| Me | CH=CH₂ | Me | H | H | H | H |
| Me | CH=CH₂ | F | H | F | H | H |
| Me | CH=CH₂ | F | H | H | F | H |
| Me | CH=CH₂ | H | F | F | H | H |
| Me | CH=CH₂ | F | H | H | H | F |
| Me | CH=CH₂ | Cl | H | Cl | H | H |
| Me | CH=CH₂ | Cl | H | H | Cl | H |
| Me | CH=CH₂ | H | Cl | Cl | H | H |
| Me | CH=CH₂ | Cl | H | H | H | Cl |
| Me | CH=CH₂ | F | H | Cl | H | H |
| Me | CH=CH₂ | Cl | H | F | H | H |
| Me | CH=CH₂ | F | H | Br | H | H |
| Me | CH=CH₂ | Br | H | F | H | H |
| Me | CH=CH₂ | H | Cl | F | H | H |
| Me | CH=CH₂ | H | F | Cl | H | H |
| Me | CH=CH₂ | F | H | Me | H | H |
| Me | CH=CH₂ | Cl | H | Me | H | H |
| Me | CH=CH₂ | Me | H | F | H | H |
| Me | CH=CH₂ | Me | H | Cl | H | H |
| Me | CH=CH₂ | H | Me | F | H | H |
| Me | CH=CH₂ | H | Me | Cl | H | H |
| Me | CH=CH₂ | H | F | Me | H | H |
| Me | CH=CH₂ | H | Cl | Me | H | H |
| Me | Et | H | H | H | H | H |
| Me | Et | H | H | F | H | H |
| Me | Et | H | F | H | H | H |
| Me | Et | F | H | H | H | H |
| Me | Et | H | H | Cl | H | H |
| Me | Et | H | Cl | H | H | H |
| Me | Et | Cl | H | H | H | H |
| Me | Et | H | H | Br | H | H |
| Me | Et | H | Br | H | H | H |
| Me | Et | Br | H | H | H | H |

-continued

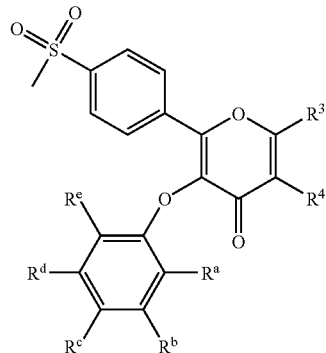

| R³ | R⁴ | Rᵃ | Rᵇ | Rᶜ | Rᵈ | Rᵉ |
|---|---|---|---|---|---|---|
| Me | Et | H | H | Me | H | H |
| Me | Et | H | Me | H | H | H |
| Me | Et | Me | H | H | H | H |
| Me | Et | F | H | F | H | H |
| Me | Et | F | H | H | F | H |
| Me | Et | F | H | H | H | F |
| Me | Et | Cl | H | Cl | H | H |
| Me | Et | Cl | H | H | Cl | H |
| Me | Et | H | Cl | Cl | H | H |
| Me | Et | Cl | H | H | H | Cl |
| Me | Et | F | H | Cl | H | H |
| Me | Et | Cl | H | F | H | H |
| Me | Et | F | H | Br | H | H |
| Me | Et | Br | H | F | H | H |
| Me | Et | H | Cl | F | H | H |
| Me | Et | H | F | Cl | H | H |
| Me | Et | F | H | Me | H | H |
| Me | Et | Cl | H | Me | H | H |
| Me | Et | Me | H | F | H | H |
| Me | Et | Me | H | Cl | H | H |
| Me | Et | H | Me | F | H | H |
| Me | Et | H | Me | Cl | H | H |
| Me | Et | H | F | Me | H | H |
| Me | Et | H | Cl | Me | H | H |
| Me | C≡CH | H | H | H | H | H |
| Me | C≡CH | H | H | F | H | H |
| Me | C≡CH | H | F | H | H | H |
| Me | C≡CH | F | H | H | H | H |
| Me | C≡CH | H | H | Cl | H | H |
| Me | C≡CH | H | Cl | H | H | H |
| Me | C≡CH | Cl | H | H | H | H |
| Me | C≡CH | H | H | Br | H | H |
| Me | C≡CH | H | Br | H | H | H |
| Me | C≡CH | Br | H | H | H | H |
| Me | C≡CH | H | H | Me | H | H |
| Me | C≡CH | H | Me | H | H | H |
| Me | C≡CH | Me | H | H | H | H |
| Me | C≡CH | F | H | F | H | H |
| Me | C≡CH | F | H | H | F | H |
| Me | C≡CH | H | F | F | H | H |
| Me | C≡CH | F | H | H | H | F |
| Me | C≡CH | Cl | H | Cl | H | H |
| Me | C≡CH | Cl | H | H | Cl | H |
| Me | C≡CH | Cl | H | H | H | Cl |
| Me | C≡CH | F | H | Cl | H | H |
| Me | C≡CH | Cl | H | F | H | H |
| Me | C≡CH | F | H | Br | H | H |
| Me | C≡CH | Br | H | F | H | H |
| Me | C≡CH | H | Cl | F | H | H |
| Me | C≡CH | H | F | Cl | H | H |
| Me | C≡CH | F | H | Me | H | H |
| Me | C≡CH | Cl | H | Me | H | H |
| Me | C≡CH | Me | H | F | H | H |
| Me | C≡CH | Me | H | Cl | H | H |
| Me | C≡CH | H | Me | F | H | H |
| Me | C≡CH | H | Me | Cl | H | H |
| Me | C≡CH | H | F | Me | H | H |

-continued

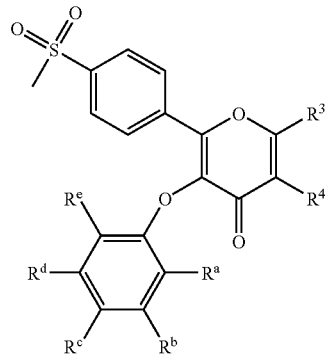

| R³ | R⁴ | Rᵃ | Rᵇ | Rᶜ | Rᵈ | Rᵉ |
|---|---|---|---|---|---|---|
| Me | C≡CH | H | Cl | Me | H | H |
| Et | Me | H | H | H | H | H |
| Et | Me | H | H | F | H | H |
| Et | Me | F | H | H | H | H |
| Et | Me | H | H | Cl | H | H |
| Et | Me | H | Cl | H | H | H |
| Et | Me | Cl | H | H | H | H |
| Et | Me | H | H | Br | H | H |
| Et | Me | H | Br | H | H | H |
| Et | Me | Br | H | H | H | H |
| Et | Me | H | H | Me | H | H |
| Et | Me | H | Me | H | H | H |
| Et | Me | Me | H | H | H | H |
| Et | Me | F | H | F | H | H |
| Et | Me | H | F | F | H | H |
| Et | Me | F | H | H | H | F |
| Et | Me | Cl | H | Cl | H | H |
| Et | Me | Cl | H | H | Cl | H |
| Et | Me | H | Cl | Cl | H | H |
| Et | Me | Cl | H | H | H | Cl |
| Et | Me | F | H | Cl | H | H |
| Et | Me | Cl | H | F | H | H |
| Et | Me | F | H | Br | H | H |
| Et | Me | Br | H | F | H | H |
| Et | Me | H | Cl | F | H | H |
| Et | Me | H | F | Cl | H | H |
| Et | Me | F | H | Me | H | H |
| Et | Me | Cl | H | Me | H | H |
| Et | Me | Me | H | F | H | H |
| Et | Me | Me | H | Cl | H | H |
| Et | Me | H | Me | F | H | H |
| Et | Me | H | Me | Cl | H | H |
| Et | Me | H | F | Me | H | H |
| Et | Me | H | Cl | Me | H | H |
| Pr | Et | H | H | H | H | H |
| Pr | Et | H | H | F | H | H |
| Pr | Et | H | F | H | H | H |
| Pr | Et | F | H | H | H | H |
| Pr | Et | H | H | Cl | H | H |
| Pr | Et | H | Cl | H | H | H |
| Pr | Et | Cl | H | H | H | H |
| Pr | Et | H | H | Br | H | H |
| Pr | Et | H | Br | H | H | H |
| Pr | Et | Br | H | H | H | H |
| Pr | Et | H | H | Me | H | H |
| Pr | Et | H | Me | H | H | H |
| Pr | Et | Me | H | H | H | H |
| Pr | Et | F | H | F | H | H |
| Pr | Et | H | F | F | H | H |
| Pr | Et | F | H | H | H | F |
| Pr | Et | Cl | H | Cl | H | H |
| Pr | Et | Cl | H | H | Cl | H |
| Pr | Et | H | Cl | Cl | H | H |
| Pr | Et | Cl | H | H | H | Cl |
| Pr | Et | F | H | Cl | H | H |
| Pr | Et | Cl | H | F | H | H |

-continued

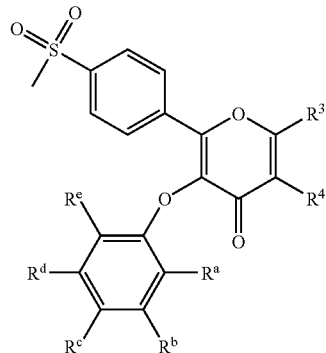

| R³ | R⁴ | Rᵃ | Rᵇ | Rᶜ | Rᵈ | Rᵉ |
|---|---|---|---|---|---|---|
| Pr | Et | F | H | Br | H | H |
| Pr | Et | Br | H | F | H | H |
| Pr | Et | H | Cl | F | H | H |
| Pr | Et | H | F | Cl | H | H |
| Pr | Et | F | H | Me | H | H |
| Pr | Et | Cl | H | Me | H | H |
| Pr | Et | Me | H | F | H | H |
| Pr | Et | Me | H | Cl | H | H |
| Pr | Et | H | Me | F | H | H |
| Pr | Et | H | Me | Cl | H | H |
| Pr | Et | H | F | Me | H | H |
| Pr | Et | H | Cl | Me | H | H |
| CH₂OH | H | H | H | H | H | H |
| CH₂OH | H | H | H | F | H | H |
| CH₂OH | H | H | F | H | H | H |
| CH₂OH | H | F | H | H | H | H |
| CH₂OH | H | H | H | Cl | H | H |
| CH₂OH | H | H | Cl | H | H | H |
| CH₂OH | H | Cl | H | H | H | H |
| CH₂OH | H | H | H | Br | H | H |
| CH₂OH | H | H | Br | H | H | H |
| CH₂OH | H | Br | H | H | H | H |
| CH₂OH | H | H | H | Me | H | H |
| CH₂OH | H | H | Me | H | H | H |
| CH₂OH | H | Me | H | H | H | H |
| CH₂OH | H | F | H | F | H | H |
| CH₂OH | H | F | H | H | F | H |
| CH₂OH | H | H | F | F | H | H |
| CH₂OH | H | F | H | H | H | F |
| CH₂OH | H | Cl | H | Cl | H | H |
| CH₂OH | H | Cl | H | H | Cl | H |
| CH₂OH | H | H | Cl | Cl | H | H |
| CH₂OH | H | Cl | H | H | H | Cl |
| CH₂OH | H | F | H | Cl | H | H |
| CH₂OH | H | Cl | H | F | H | H |
| CH₂OH | H | F | H | Br | H | H |
| CH₂OH | H | Br | H | F | H | H |
| CH₂OH | H | H | Cl | F | H | H |
| CH₂OH | H | H | F | Cl | H | H |
| CH₂OH | H | F | H | Me | H | H |
| CH₂OH | H | Cl | H | Me | H | H |
| CH₂OH | H | Me | H | F | H | H |
| CH₂OH | H | Me | H | Cl | H | H |
| CH₂OH | H | H | Me | F | H | H |
| CH₂OH | H | H | Me | Cl | H | H |
| CH₂OH | H | H | F | Me | H | H |
| CH₂OH | H | H | Cl | Me | H | H |
| CH₂OCH₃ | H | H | H | H | H | H |
| CH₂OCH₃ | H | H | H | F | H | H |
| CH₂OCH₃ | H | H | F | H | H | H |
| CH₂OCH₃ | H | F | H | H | H | H |
| CH₂OCH₃ | H | H | H | Cl | H | H |
| CH₂OCH₃ | H | H | Cl | H | H | H |
| CH₂OCH₃ | H | Cl | H | H | H | H |
| CH₂OCH₃ | H | H | H | Br | H | H |
| CH₂OCH₃ | H | H | Br | H | H | H |
| CH₂OCH₃ | H | Br | H | H | H | H |
| CH₂OCH₃ | H | H | H | Me | H | H |
| CH₂OCH₃ | H | H | Me | H | H | H |

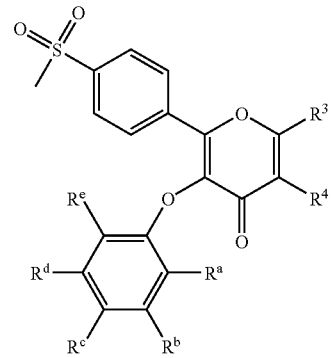

| R³ | R⁴ | Rᵃ | Rᵇ | Rᶜ | Rᵈ | Rᵉ |
|---|---|---|---|---|---|---|
| CH₂OCH₃ | H | Me | H | H | H | H |
| CH₂OCH₃ | H | F | H | F | H | H |
| CH₂OCH₃ | H | F | H | H | F | H |
| CH₂OCH₃ | H | H | F | F | H | H |
| CH₂OCH₃ | H | F | H | H | H | F |
| CH₂OCH₃ | H | Cl | H | Cl | H | H |
| CH₂OCH₃ | H | Cl | H | H | Cl | H |
| CH₂OCH₃ | H | H | Cl | Cl | H | H |
| CH₂OCH₃ | H | Cl | H | H | H | Cl |
| CH₂OCH₃ | H | F | H | Cl | H | H |
| CH₂OCH₃ | H | Cl | H | F | H | H |
| CH₂OCH₃ | H | F | H | Br | H | H |
| CH₂OCH₃ | H | Br | H | F | H | H |
| CH₂OCH₃ | H | H | Cl | F | H | H |
| CH₂OCH₃ | H | H | F | Cl | H | H |
| CH₂OCH₃ | H | F | H | Me | H | H |
| CH₂OCH₃ | H | Cl | H | Me | H | H |
| CH₂OCH₃ | H | Me | H | F | H | H |
| CH₂OCH₃ | H | Me | H | Cl | H | H |
| CH₂OCH₃ | H | H | Me | F | H | H |
| CH₂OCH₃ | H | H | Me | Cl | H | H |
| CH₂OCH₃ | H | H | F | Me | H | H |
| CH₂OCH₃ | H | H | Cl | Me | H | H |
| CF₂H | H | H | H | H | H | H |
| CF₂H | H | H | H | F | H | H |
| CF₂H | H | H | F | H | H | H |
| CF₂H | H | F | H | H | H | H |
| CF₂H | H | H | H | Cl | H | H |
| CF₂H | H | H | Cl | H | H | H |
| CF₂H | H | Cl | H | H | H | H |
| CF₂H | H | H | H | Br | H | H |
| CF₂H | H | H | Br | H | H | H |
| CF₂H | H | Br | H | H | H | H |
| CF₂H | H | H | H | Me | H | H |
| CF₂H | H | H | Me | H | H | H |
| CF₂H | H | Me | H | H | H | H |
| CF₂H | H | F | H | F | H | H |
| CF₂H | H | F | H | H | F | H |
| CF₂H | H | H | F | F | H | H |
| CF₂H | H | F | H | H | H | F |
| CF₂H | H | Cl | H | Cl | H | H |
| CF₂H | H | Cl | H | H | Cl | H |
| CF₂H | H | H | Cl | Cl | H | H |
| CF₂H | H | Cl | H | H | H | Cl |
| CF₂H | H | F | H | Cl | H | H |
| CF₂H | H | Cl | H | F | H | H |
| CF₂H | H | F | H | Br | H | H |
| CF₂H | H | Br | H | F | H | H |
| CF₂H | H | H | Cl | F | H | H |
| CF₂H | H | H | F | Cl | H | H |
| CF₂H | H | F | H | Me | H | H |
| CF₂H | H | Cl | H | Me | H | H |
| CF₂H | H | Me | H | F | H | H |
| CF₂H | H | Me | H | Cl | H | H |
| CF₂H | H | H | Me | F | H | H |
| CF₂H | H | H | Me | Cl | H | H |
| CF₂H | H | H | F | Me | H | H |
| CF₂H | H | H | Cl | Me | H | H |
| CF₂H | Br | F | H | F | H | H |

-continued

| R³ | R⁴ | Rᵃ | Rᵇ | Rᶜ | Rᵈ | Rᵉ |
|---|---|---|---|---|---|---|
| CF₂H | Me | F | H | F | H | H |
| CH₂OCH₂CH₃ | H | H | H | F | H | H |
| CH₂OCH₂CH₃ | H | H | H | Cl | H | H |
| CH₂OCH₂CH₃ | H | F | H | F | H | H |
| CH₂OCH₂CH₂CH₃ | H | H | H | F | H | H |
| CH₂OCH₂CH₂CH₃ | H | H | H | Cl | H | H |
| CH₂OCH₂CH₂CH₃ | H | F | H | F | H | H |
| CH₂OCH(CH₃)₂ | H | H | H | F | H | H |
| CH₂OCH(CH₃)₂ | H | H | H | Cl | H | H |
| CH₂OCH(CH₃)₂ | H | F | H | F | H | H |
| CH₂OCH₂CH=CH₂ | H | H | H | F | H | H |
| CH₂OCH₂CH=CH₂ | H | H | H | Cl | H | H |
| CH₂OCH₂CH=CH₂ | H | F | H | F | H | H |
| O-cyclopropyl | H | H | H | F | H | H |
| O-cyclopropyl | H | H | H | Cl | H | H |
| O-cyclopropyl | H | F | H | F | H | H |
| O-cyclobutyl | H | H | H | F | H | H |
| O-cyclobutyl | H | H | H | Cl | H | H |
| O-cyclobutyl | H | F | H | F | H | H |
| OCH₂-cyclopropyl | H | H | H | F | H | H |
| OCH₂-cyclopropyl | H | H | H | Cl | H | H |
| OCH₂-cyclopropyl | H | F | H | F | H | H |
| CH₂OCOCH₃ | H | H | H | H | H | H |
| CH₂OCOCH₃ | H | H | H | F | H | H |
| CH₂OCOCH₃ | H | H | F | H | H | H |
| CH₂OCOCH₃ | H | F | H | H | H | H |
| CH₂OCOCH₃ | H | H | H | Cl | H | H |
| CH₂OCOCH₃ | H | H | Cl | H | H | H |
| CH₂OCOCH₃ | H | Cl | H | H | H | H |
| CH₂OCOCH₃ | H | H | H | Br | H | H |
| CH₂OCOCH₃ | H | H | Br | H | H | H |
| CH₂OCOCH₃ | H | Br | H | H | H | H |
| CH₂OCOCH₃ | H | Me | H | H | H | H |
| CH₂OCOCH₃ | H | F | H | F | H | H |
| CH₂OCOCH₃ | H | F | H | H | F | H |
| CH₂OCOCH₃ | H | H | F | F | H | H |
| CH₂OCOCH₃ | H | F | H | H | H | F |
| CH₂OCOCH₃ | H | Cl | H | Cl | H | H |
| CH₂OCOCH₃ | H | Cl | H | H | Cl | H |
| CH₂OCOCH₃ | H | H | Cl | Cl | H | H |
| CH₂OCOCH₃ | H | Cl | H | H | H | Cl |
| CH₂OCOCH₃ | H | F | H | Cl | H | H |
| CH₂OCOCH₃ | H | Cl | H | F | H | H |
| CH₂OCOCH₃ | H | F | H | Br | H | H |
| CH₂OCOCH₃ | H | Br | H | F | H | H |
| CH₂OCOCH₃ | H | H | Cl | F | H | H |
| CH₂OCOCH₃ | H | H | F | Cl | H | H |
| CH₂OCOCH₃ | H | Me | H | F | H | H |
| CH₂OCOCH₃ | H | Me | H | Cl | H | H |
| COOH | H | H | H | H | H | H |
| COOH | H | H | H | F | H | H |
| COOH | H | H | F | H | H | H |
| COOH | H | F | H | H | H | H |
| COOH | H | H | H | Cl | H | H |
| COOH | H | H | Cl | H | H | H |
| COOH | H | Cl | H | H | H | H |
| COOH | H | H | H | Br | H | H |
| COOH | H | H | Br | H | H | H |
| COOH | H | Br | H | H | H | H |
| COOH | H | Me | H | H | H | H |
| COOH | H | F | H | F | H | H |
| COOH | H | F | H | H | F | H |
| COOH | H | H | F | F | H | H |
| COOH | H | F | H | H | H | F |
| COOH | H | Cl | H | Cl | H | H |
| COOH | H | Cl | H | H | Cl | H |
| COOH | H | H | Cl | Cl | H | H |
| COOH | H | Cl | H | H | H | Cl |
| COOH | H | F | H | Cl | H | H |
| COOH | H | Cl | H | F | H | H |
| COOH | H | F | H | Br | H | H |
| COOH | H | Br | H | F | H | H |
| COOH | H | H | Cl | F | H | H |
| COOH | H | H | F | Cl | H | H |
| COOH | H | Me | H | F | H | H |
| COOH | H | Me | H | Cl | H | H |

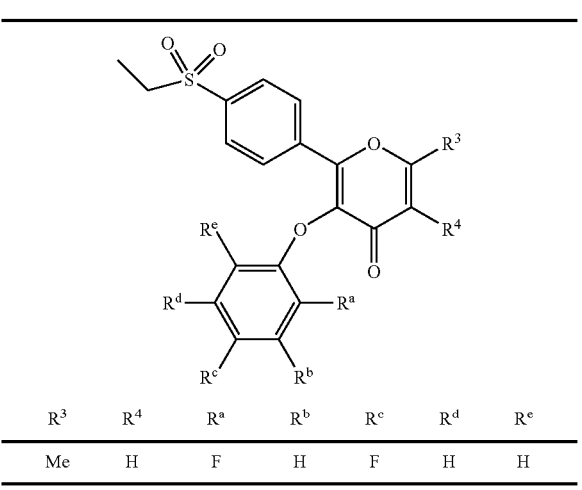

| $R^3$ | $R^4$ | $R^a$ | $R^b$ | $R^c$ | $R^d$ | $R^e$ |
|---|---|---|---|---|---|---|
| Me | H | F | H | F | H | H | and pharmaceutically acceptable salts thereof.

Of outstanding interest are:

3-(4-fluoro-2-methylphenoxy)-2-(4-methanesulfonylphenyl)-6-methylpyran-4-one;

3-(4-chloro-2-methylphenoxy)-2-(4-methanesulfonylphenyl)-6-methylpyran-4-one;

3-(2-chloro-4-methylphenoxy)-2-(4-methanesulfonylphenyl)-6-methylpyran-4-one;

3-(2-bromophenoxy)-2-(4-methanesulfonylphenyl)-6-methylpyran-4-one;

3-(3-bromophenoxy)-2-(4-methanesulfonylphenyl)-6-methylpyran-4-one;

3-(4-bromo-2-fluorophenoxy)-2-(4-methanesulfonylphenyl)-6-methylpyran-4-one;

3-(4-bromo-2-chlorophenoxy)-2-(4-methanesulfonylphenyl)-6-methylpyran-4-one;

3-(2,4-dibromophenoxy)-2-(4-methanesulfonylphenyl)-6-methylpyran-4-one;

3-(2,4-difluorophenoxy)-2-(4-ethanesulfonylphenyl)-6-methylpyran-4-one 2-(4-methanesulfonylphenyl)-6-methyl-3-(2-methylphenoxy)pyran-4-one;

2-(4-methanesulfonylphenyl)-6-methyl-3-(3-methylphenoxy)pyran-4-one;

3-(2-fluoro-4-methylphenoxy)-2-(4-methanesulfonylphenyl)-6-methylpyran-4-one;

3-(2,4-difluorophenoxy)-6-ethyl-2-(4-methanesulfonylphenyl)-5-methylpyran-4-one;

3-chloro-5-(2,4-difluorophenoxy)-6-(4-methanesulfonylphenyl)-2-methylpyran-4-one;

3-chloro-5-(4-fluorophenoxy)-6-(4-methanesulfonylphenyl)-2-methylpyran-4-one;

3-chloro-5-(4-chlorophenoxy)-6-(4-methanesulfonylphenyl)-2-methylpyran-4-one;

3-bromo-5-(2,4-difluorophenoxy)-6-(4-methanesulfonylphenyl)-2-methylpyran-4-one;

3-bromo-5-(4-chlorophenoxy)-6-(4-methanesulfonylphenyl)-2-methylpyran-4-one;

3-(2,4-difluorophenoxy)-5,6-dimethyl-2-(4-methanesulfonylphenyl)pyran-4-one;

3-(2,4-difluorophenoxy)-2-(4-methanesulfonylphenyl)-6-methyl-5-vinyl pyran-4-one;

3-(2,4-difluorophenoxy)-5-ethyl-2-(4-methanesulfonylphenyl)-6-methylpyran-4-one;

3-(2,4-difluorophenoxy)-6-hydroxymethyl-2-(4-methanesulfonylphenyl) pyran-4-one;

3-(4-fluorophenoxy)-6-hydroxymethyl-2-(4-methanesulfonylphenyl)pyran-4-one;

3-(4-chlorophenoxy)-6-hydroxymethyl-2-(4-methanesulfonylphenyl)pyran-4-one;

3-(2-fluoro-4-bromophenoxy)-6-hydroxymethyl-2-(4-methanesulfonyl phenyl)pyran-4-one;

3-(2,4-difluorophenoxy)-2-(4-methanesulfonylphenyl)-6-methoxymethyl pyran-4-one;

3-(4-fluorophenoxy)-2-(4-methanesulfonylphenyl)-6-methoxymethylpyran-4-one;

3-(4-chlorophenoxy)-2-(4-methanesulfonylphenyl)-6-methoxymethylpyran-4-one;

acetic acid [5-(2,4-difluorophenoxy)-6-(4-methanesulfonylphenyl)-4-oxo-4H-pyran-2-yl]methyl ester;

acetic acid [5-(4-fluorophenoxy)-6-(4-methanesulfonylphenyl)-4-oxo-4H-pyran-2-yl]methyl ester;

acetic acid [5-(4-chlorophenoxy)-6-(4-methanesulfonylphenyl)-4-oxo-4H-pyran-2-yl]methyl ester;

5-(2,4-difluorophenoxy)-6-(4-methanesulfonylphenyl)-4-oxo-4H-pyran-2-carboxylic acid;

5-(4-chlorophenoxy)-6-(4-methanesulfonylphenyl)-4-oxo-4H-pyran-2-carboxylic acid;

6-(1,1-difluoromethyl)-3-(2,4-difluorophenoxy)-2-(4-methanesulfonylphenyl)pyran-4-one;

6-(1,1-difluoromethyl)-3-(4-bromophenoxy)-2-(4-methanesulfonylphenyl)pyran-4-one;

6-(1,1-difluoromethyl)-2-(4-methanesulfonylphenyl)-3-(4-methylphenoxy)pyran-4-one;

3-bromo-2-(1,1-difluoromethyl)-5-(2,4-difluorophenoxy)-6-(4-methanesulfonylphenyl)pyran-4-one;

2-(1,1-difluoromethyl)-5-(2,4-difluorophenoxy)-6-(4-methanesulfonylphenyl)-3-methylpyran-4-one;

and pharmaceutically acceptable salts thereof.

The present invention also provides processes for preparing a compound of formula (I) which depend on the definition of $R^3$ and $R^4$. When $R^3$ is an alkyl group and $R^4$ is a hydrogen atom or an alkyl group, compounds of formula (I) are prepared according to the definition of $R^1$. Thus, compounds of formula (I) in which $R^3$ is a methyl group, $R^4$ is a hydrogen atom and $R^1$ is an alkyl or —$NR^5R^6$ group in which $R^5$ and $R^6$ are alkyl groups, viz. a 2-phenylpyran-4-one derivative of formula (II):

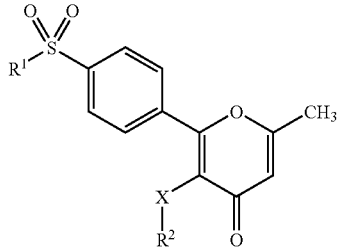
(II)

wherein $R^{1a}$ is an alkyl or —$NR^{5a}R^{6a}$ group in which $R^{5a}$ and $R^{6a}$ are each independently alkyl groups, and $R^2$ and X are as defined above, which comprises reacting a carbonyl derivative of formula (III):

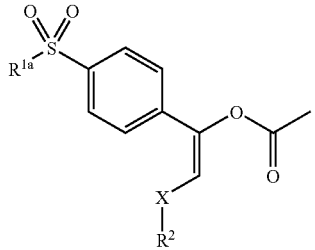
(III)

wherein $R^{1a}$, $R^2$ and X are as defined above with an excess of anhydrous acetic acid or acetic anhydride and polyphosphoric acid, at a temperature from 90° C. to 150° C.

The compound of formula (II) may also be prepared by reacting a vinyl derivative of formula (IV):

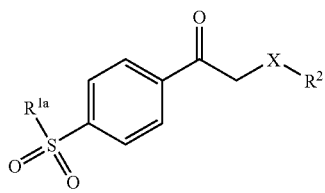
(IV)

wherein $R^{1a}$, $R^2$ and X are as defined above, with an excess of acetic anhydride and polyphosphoric acid at a temperature from 80° C. to 120° C.

The vinyl derivative of formula (IV) may be obtained by reacting a carbonyl derivative of formula (III) with acetic anhydride and methanesulfonic acid at a temperature from 50° C. to 100° C.

The carbonyl derivative of formula (III) may be obtained by methods well known in the literature (EP-A-714883; WO 96/06840; WO 96/31509 and DE-2064520) or when X represents an oxygen or sulfur atom, by reacting a phenacyl derivative of formula (V):

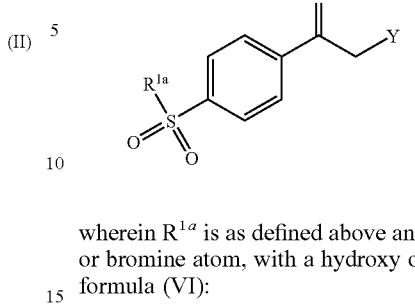
(V)

wherein $R^{1a}$ is as defined above and Y represents a chlorine or bromine atom, with a hydroxy or mercapto derivative of formula (VI):

$$HX^a—R^2 \quad (VI)$$

wherein $R^2$ is as defined above and $X^a$ is an oxygen or sulfur atom.

The reaction between the phenacyl derivative of formula (V) and the alcohol or thiol of formula (VI) may be carried out by heating a mixture of these two starting materials, optionally in a solvent mixture of methylene chloride, benzene or toluene and water, at a temperature of from 15° C. to 30° C. and in the presence of a phase transfer catalyst such as benzyltriethylamonium chloride.

The carbonyl derivative of formula (III) in which X is other than a sulfur atom, may also be prepared by reacting a thio derivative of formula (VII):

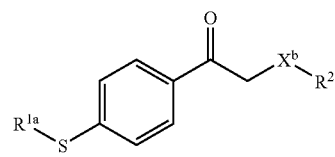
(VII)

wherein $R^{1a}$ and $R^2$ are as defined above, and $X^b$ is a single bond, an oxygen atom or a methylene group, with an oxidizing agent, preferably magnesium monoperoxyphthalate or 3-chloroperoxybenzoic acid. The reaction is preferably carried out in an organic solvent such as a mixture of methylene chloride with methanol or ethanol, at a temperature from 10° C. to 40° C.

The present invention also provides a process for the preparation of compound of formula (I) wherein $R^3$ and $R^4$ are alkyl groups and $R^1$ is an alkyl or —$NR^5R^6$ group in which $R^5$ and $R^6$ are alkyl group, viz. 2-phenylpyran-4-one derivative of formula (VIII):

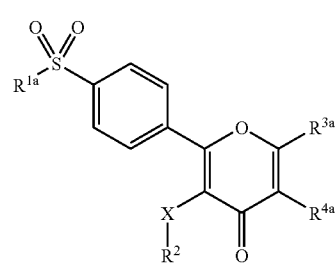
(VIII)

wherein $R^{4a}$ is an alkyl group, $R^{3a}$ represents a $CH_2$—$R^{4a}$ group and $R^{1a}$, $R^2$ and X are as defined above, which comprises reacting a carbonyl derivative of formula (III) with an excess of an anhydride of formula (IX):

  (IX)

or a carboxylic acid of formula (X):

  (X)

and polyphosphoric acid at a temperature from 90° C. to 150° C.

The compound of formula (VIII) can also be obtained by reacting a vinyl derivative of formula (XI):

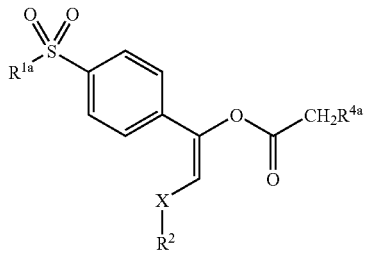  (XI)

wherein $R^{1a}$, $R^2$, $R^{4a}$ and X are as defined above with an excess of an anhydride of formula (IX) and polyphosphoric acid at a temperature from 90° C. to 150° C. The vinyl derivative of formula (XI) may be prepared by reacting a carbonyl derivative of formula (III) with an anhydride of formula (IX) and methanesulfonic acid at a temperature from 50° C. to 100° C.

The present invention also provides a process for the preparation of a compound of formula (I) wherein $R^3$ is a alkyl group, $R^4$ is a hydrogen atom, or an alkyl group, $R^1$ is an alkyl group, and X is other than a sulfur atom viz. 2-phenylpyran-4-one derivative of formula (XII):

(XII)

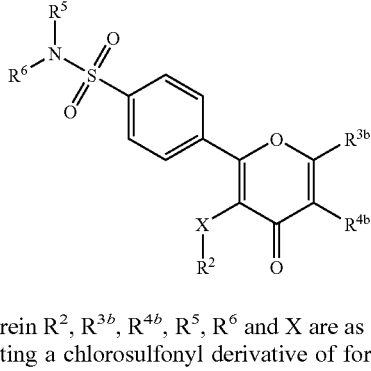

wherein $R^{1b}$ is an alkyl group, $R^{3b}$ is a methyl group or a $R^{4b}CH_2$ group, $R^{4b}$ is a hydrogen atom or an alkyl group and $R^2$ and $X^b$ are as defined above by reacting a mercapto derivative of formula (XIII):

(XIII)

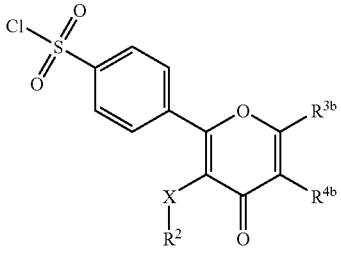

wherein $R^{1b}$, $R^{3b}$, $R^{4b}$, $R^2$ and $X^b$ are as defined above with an oxidizing agent, preferably with magnesium monoperoxyphthalate or 3-chloroperoxybenzoic acid.

The reaction between the mercapto derivative of formula (XIII) and the oxidizing agent is preferably carried out, as previously disclosed for the compound of formula (VII), in an organic solvent such as a mixture of methylene chloride with methanol or ethanol, at a temperature of from 10° C. to 40° C.

The present invention additionally provides a process for the preparation of a compound of formula (I) wherein $R^1$ is a —$NR^5R^6$ group, $R^3$ is an alkyl group and $R^4$ is a hydrogen atom, or an alkyl group viz. 2-phenylpyran-4-one derivative of formula (XIV):

(XIV)

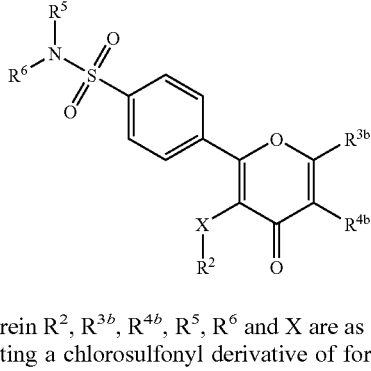

wherein $R^2$, $R^{3b}$, $R^{4b}$, $R^5$, $R^6$ and X are as defined above by reacting a chlorosulfonyl derivative of formula (XV):

(XV)

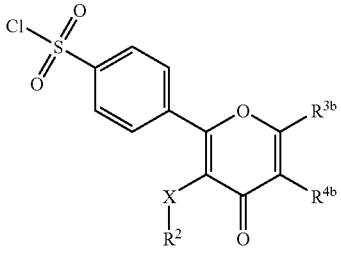

wherein $R^2$, $R^{3b}$, $R^{4b}$ and X are as defined above with an amine of formula (XVI):

  (XVI)

wherein $R^5$ and $R^6$ are as defined above.

This reaction is preferably carried out at a temperature of from 10° C. to 40° C.

The chlorosulfonyl derivative of formula (XV) may, for example, be prepared by reacting a compound of formula (XVII):

(XVII)

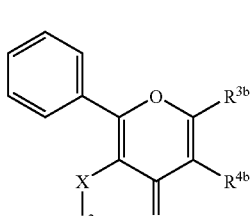

wherein $R^2$, $R^{3b}$, $R^{4b}$ and X are as defined above with chlorosulfonic acid, preferably at a temperature of from 80° C. to 120° C.

The present invention further provides a process for the preparation of a compound of formula (I) wherein $R^3$ is an alkyl group, $R^4$ is an hydrogen atom or an alkyl group and $R^1$ is a —$NR^5R^6$ group wherein $R^5$ and $R^6$ are hydrogen, viz, the 2-phenylpyran-4-one derivative of formula (XVIII):

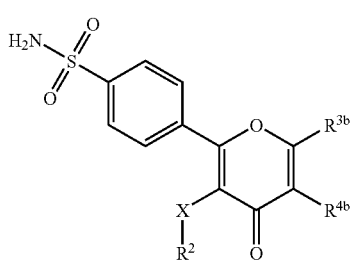

(XVIII)

wherein $R^2$, $R^{3b}$, $R^{4b}$ and X are as defined above by debenzylation of the corresponding N,N-dibenzyl derivative of formula (XIX):

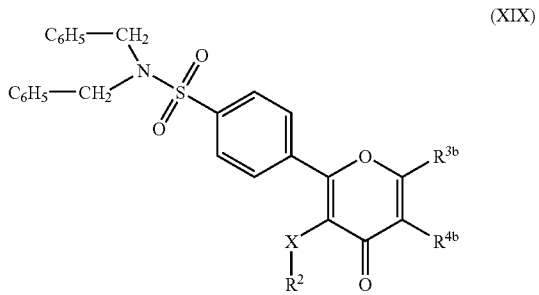

(XIX)

wherein $R^2$, $R^{3b}$, $R^{4b}$ and X are as defined above.

The debenzylation is preferably carried out with an excess of trifluoroacetic, sulfuric or methanesulfonic acid at a temperature of from 0° C. to 120° C.

The intermediate of formula (XIX) may be prepared according to the above processes using appropriate starting materials wherein $R^5$ and $R^6$ (or $R^{5a}$ and $R^{6a}$) both represent benzyl groups.

The intermediate of formula (V) and (VII) used in the preparation of the compounds of the invention may be prepared by methods disclosed in the literature, for example, in M. F. Saettone, J. Org. Chem. 31, p. 1959 (1966) and WO 96/06840.

The intermediate compounds of formula (XIII) and (XVII) may be prepared by the same process disclosed for the preparation of compounds of formula (II) and (VIII), with the appropriate starting materials.

The 2-phenylpyran-4-one derivatives of formula (I) wherein $R^3$ is other than an alkyl group and $R^4$ is a hydrogen atom, viz. 2-phenylpyran-4-one derivatives of formula (XX):

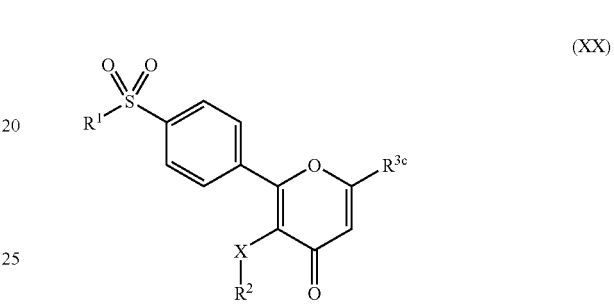

(XX)

wherein $R^{3c}$ is a hydroxymethyl, alkoxymethyl, $C_3$-$C_7$ cycloalkoxymethyl, alkenylmethoxymethyl, $C_3$-$C_7$ cycloalkylmethoxymethyl, benzyloxy methyl, hydroxycarbonyl, nitrile, trifluoromethyl, difluoromethyl group, or a $CH_2OCOR^7$ group, wherein $R^7$ is an alkyl or a phenyl group, and $R^1$, X and $R^2$ are as defined above, can be prepared by processes which are represented in the following scheme:

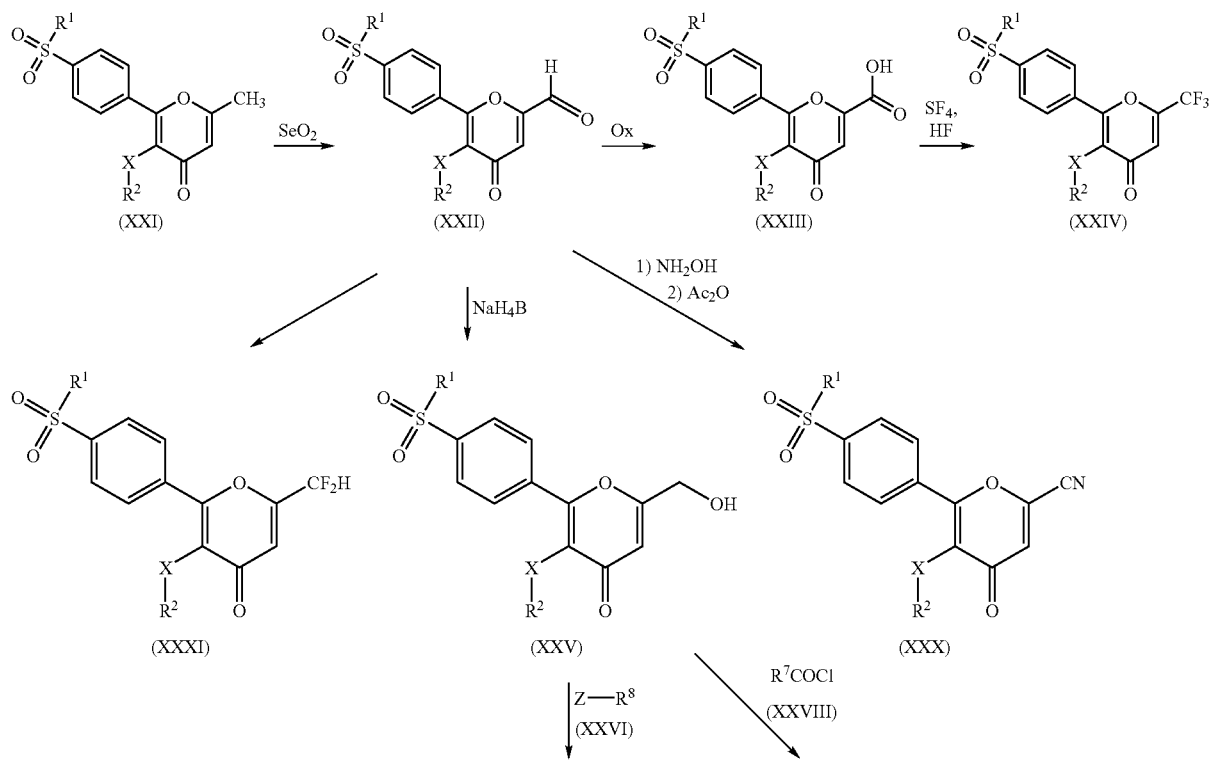

-continued

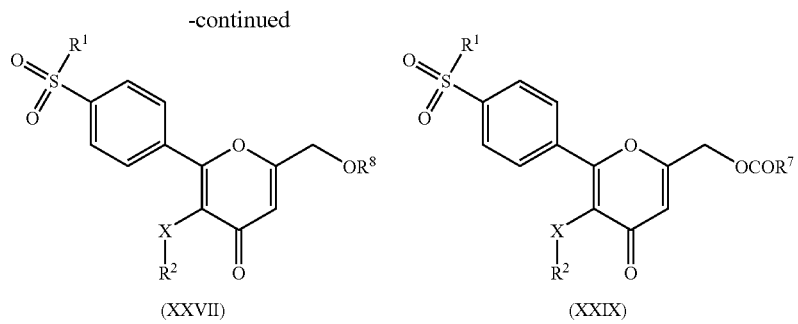

As it can be seen in the scheme, 2-phenylpyran-4-one derivatives of general formula (XX), are prepared from compounds of formula (I) in which $R^3$ is a methyl group and $R^4$ is a hydrogen atom, viz. compound of formula (XXI), which processes of preparation have been disclosed above. In a first stage, compounds of formula (XXI) are treated with an oxidizing agent as selenium dioxide in an organic solvent as tetrahydrofuran or dioxan, in a pressure vessel and at a temperature from 100° C. to 190° C. The corresponding aldehyde of formula (XXII) is obtained, which is used as starting material to obtain the compounds of general formula (XX).

The compounds of formula (XX) wherein $R^{3c}$ is a hydroxycarbonyl group, viz. compound of formula (XXIII), are prepared from the corresponding aldehyde (XXII) by reaction with an oxidizing agent as pyridinium dichromate or chromium (IV) oxide in an organic solvent such as N,N-dimethylformamide, ethanol or acetone/sulfuric acid, at a temperature between −5° C. and 35° C. The obtained compounds (XXIII) are used as starting materials to obtain compounds of formula (I) wherein $R^{3c}$ is a trifluoromethyl group, viz. compound of formula (XXIV). The reaction is carried out by reaction of compounds (XXIII) with a mixture of sulphur tetrafluoride and hydrogen fluoride, optionally in the presence of an organic solvent such as methylene chloride, in a pressure vessel, and at a temperature from 20° C. to 140° C.

The compounds of formula (XX) wherein $R^{3c}$ represents a hydroxymethyl group, viz. compounds of formula (XXV) are prepared by reduction of compounds of formula (XXII) with a boron or aluminium hydride, preferably sodium borohydride in a solvent as methanol or ethanol and at a temperature from 10° C. to 40° C. Further reaction of compounds of formula (XXV) with an appropriate halide of formula (XXVI):

wherein Z represents a chlorine, bromine or iodine atom and $R^8$ represents an alkyl, $C_3$-$C_7$ cycloalkyl, alkenylmethyl, $C_3$-$C_7$ cycloalkylmethyl, or benzyl group, provide the compounds of formula (XX) wherein $R^{3c}$ is an alkoxymethyl, $C_3$-$C_7$ cycloalkoxymethyl, alkenylmethoxymethyl, $C_3$-$C_7$ cycloalkylmethoxymethyl or benzyloxymethyl group, viz. compounds of formula (XXVII). The reaction is carried out in an organic solvent as acetone, N,N-dimethylformamide or tetrahydrofuran in the presence of sodium or potassium hydride or amide, and at a temperature between 20° C. and 120° C.

Further more, the reaction of compounds of formula (XXV) with an appropriate acyl halide of formula (XXVIII):

wherein $R^7$ represents an alkyl or a phenyl group provide compounds of formula (XXIX). The reaction is carried out in an organic solvent such as tetrahydrofuran, methylene chloride, chloroform or dioxane in the presence of a tertiary amine, such as triethylamine, at a temperature from 20° C. to the boiling point of the solvent.

Also aldehydes of formula (XXII) are used as starting material to obtain compounds of formula (XX) wherein $R^{3c}$ is a nitrile group, viz. compounds of formula (XXX). The reaction is carried out in a first stage by treatment of aldehydes (XXII) with hydroxylamine hydrochloride and formic acid at a temperature from 80° C. to 120° C. The resulting oxime derivative is isolated and heated with an excess of acetic anhydride at a temperature between 100° C. to 180° C.

The compounds of formula (XX) wherein $R^{3c}$ represents a difluoromethyl group, viz. compounds of formula (XXXI), are prepared from aldehydes of formula (XXII) by reaction with a fluorinated reagent as diethylaminosulfur trifluoride or a mixture of sulfur tetrafluoride-hydrogen fluoride, optionally in the presence of an organic solvent such as methylene chloride, benzene or toluene and at a temperature from 0° C. to 130° C.

The present invention also provides a process for the preparation of compound of formula (I) wherein $R^4$ is other than a hydrogen atom, viz. 2-phenylpyran-4-one derivative of formula (XXXII):

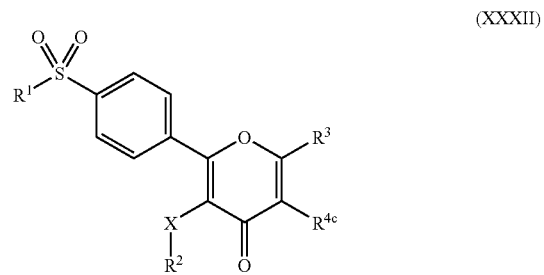

wherein $R^{4c}$ is an alkyl, alkenyl or alkynyl group and $R^1$, $R^2$, $R^3$ and X are as defined above, which comprises reacting a compound of formula (XXXIII):

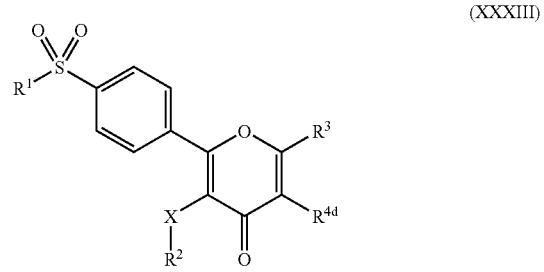

wherein $R^{4d}$ is a chlorine, bromine or iodine atom, preferably a bromine atom and $R^1$, $R^2$, $R^3$ and X are as defined above, with a tin derivative of formula (XXXIV):

$$R^{4c}Sn(R^9)_3 \qquad (XXXIV)$$

wherein $R^{4c}$ is as defined above and $R^9$ is an alkyl group. The reaction is carried out in a solvent such as dimethylformamide, tetrahydrofuran or dioxane, in the presence of a tertiary amine, such as triethylamine, with tri-o-tolylphosphine and palladium (II) acetate, and at a temperature from 20° C. to 150° C.

The derivative of formula (XXXIII), wherein $R^{4d}$ is preferably a bromine atom, may be obtained by reacting a derivative of formula (XX) or a derivative of formula (XXI) with bromine or pyridinium tribromide, in an organic solvent such as 1,1,2,2-tetrachloroethane, methylene chloride or chloroform, in a pressure vassel, and at a temperature from 20° C. to 180° C.

The 2-phenylpyran-4-one derivatives of formula (I) in which there is the presence of a basic group, can be converted by methods known per se into pharmaceutically acceptable salts, preferably acid addition salts by treatment with organic or inorganic acids as fumaric, tartaric, succinic or hydrochloric acid. Also, 2-phenylpyran-4-one derivatives of formula (I) in which $R^3$ represents an hydroxycarbonyl group, may be converted into pharmacologically acceptable salts with, for instance, alkali metals such as sodium or potassium by reaction with an alkali metal hydroxide.

The following biological tests and data further illustrate this invention.

COX-1 and COX-2 Activities in Human Whole Blood

Fresh blood from healthy volunteers who had not taken any non-steroidal anti-inflammatory drugs for at least 7 days prior to blood extraction was collected in heparinized tubes (20 units of heparin per ml). For the COX-1 activity determination, 500:1 aliquots of blood were incubated with either 5:1 vehicle (dimethylsulphoxide) or 5:1 of a test compound for 1 h at 37° C. Calcium ionophore A23187 (25:M) was added 20 min before stopping the incubation. Plasma was separated by centrifugation (10 min at 13000 rpm) and kept at −30° C. until $TXB_2$ levels were measured using an enzyme immunoassay kit (ELISA).

The effect of the compounds was evaluated by incubating each compound at five to six different concentrations with triplicate determinations. $IC_{50}$ values were obtained by non-linear regression using InPlot, GraphPad software on an IBM computer.

For the COX-2 activity determination, 500:1 aliquots of blood were incubated in the presence of LPS (10:g/ml) for 24 h at 37° C. in order to induce the COX-2 expression (Patriagnani et al., J. Pharm. Exper. Ther. 271; 1705-1712 (1994)). Plasma was separated by centrifugation (10 min at 13000 rpm) and kept at −30° C. until $PGE_2$ levels were measured using an enzyme immunoassay kit (ELISA). The effects of inhibitors were studied by incubating each compound (5:1 aliquots) at five to six different concentrations with triplicate determinations in the presence of LPS for 24 hours. $IC_{50}$ values were obtained by non-linear regression using InPlot, GraphPad software on an IBM computer.

The results obtained from the biological assays are shown in Table 1.

TABLE 1

| | COX-1 and COX-2 Inhibition | | |
|---|---|---|---|
| Example | COX-1 $IC_{50}$ (μM) | COX-2 $IC_{50}$ (μM) | Ratio COX-1/COX-2 |
| 1 | 21.2 | 0.18 | 118 |
| 2 | 38.5 | 0.13 | 296 |
| 3 | 16.3 | 0.24 | 68 |
| 6 | 40.2 | 0.15 | 268 |
| 7 | 33.4 | 0.21 | 159 |
| 8 | 57.5 | 1.13 | 51 |
| 10 | 19.9 | 0.086 | 231 |
| 11 | 14.2 | 0.30 | 47 |
| 16 | 26.0 | 0.53 | 74 |
| 17 | 20.0 | 0.78 | 27 |
| 18 | 76.7 | 0.82 | 93 |
| 19 | 14.6 | 0.082 | 178 |
| 20 | 31.2 | 1.43 | 22 |
| 21 | 35.6 | 0.58 | 62 |
| 22 | 53.0 | 0.19 | 279 |
| 23 | 2% at 100 μM | 1.44 | >70 |
| 24 | 13% at 100 μM | 0.60 | >150 |
| 26 | 21.1 | 0.17 | 124 |
| 27 | 86.3 | 0.32 | 270 |
| 28 | 91.9 | 0.44 | 209 |
| 30 | 50.3 | 0.14 | 359 |
| 31 | 17% at 100 μM | 1.10 | >90 |
| 32 | 450 | 0.42 | 1070 |
| 36 | 28.5 | 0.097 | 294 |
| Indomethacin | 0.19 | 0.22 | 0.86 |

Indomethacin is 1-(4-chlorobenzoyl)-5-methoxy-2-methylindole-3-acetic acid.

As shown in Table 1, the 2-phenylpyran-4-one derivatives of formula (I) are potent and selective COX-2 inhibitors whereas the reference compound indomethacin is as equipotent as COX-2 and COX-1 inhibitor. Thus the compounds of the invention are preferably selective inhibitors of mammalian COX-2, for example human COX-2.

The compounds of the invention also preferably have low inhibitory activity toward mammalian COX-1, for example human COX-1. Inhibitory activity can typically be measured by in vitro assays, for example as described above.

Preferred compounds of the invention have an $IC_{50}$ value for COX-2 of less than 5:M, preferably less than 3 more preferably less than 2.5:M. Preferred compounds of the invention also have an $IC_{50}$ value for COX-1 of greater than 10:M, preferably greater than 20:M. As an indicator of selectivity for inhibition of COX-2 over COX-1, the ratio of COX-1/COX-2 $IC_{50}$ values is preferably greater than 20, 30 or 50, more preferably greater than 60, 100 or 200.

The present invention further provides a compound of formula (I) for use in a method of treatment of the human or animal body by therapy, in particular for the treatment of pain, fever or inflammation, to inhibit prostanoid-induced smooth muscle contraction or for the prevention or treatment of colorectal cancer or neurodegenerative diseases, for example, Alzheimer disease.

The present invention further provides the use of a compound of formula (I) in the manufacture of a medicament for the treatment of pain, fever or inflammation, to inhibit prostanoid-induced smooth muscle contraction or for the prevention or treatment of colorectal cancer.

The compounds of formula (I) are useful for relief of pain, fever and inflammation of a variety of conditions including rheumatic fever, symptoms associated with influenza or other viral infections, common cold, low back and neck pain, dysmenorrhoea, headache, toothache, sprains and strains, myositis, neuralgia, synovitis, bursitis, tendinitis, injuries, following surgical and dental procedures and arthritis including rheumatoid arthritis, osteoarthritis, gouty arthritis, spondyloarthopathies, systemic lupus erythematosus and juvenile arthritis. They may also be used in the treatment of skin inflammation disorders such as psoriasis, eczema, burning and dermatitis. In addition, such compounds may be used for the prevention or treatment of colorectal cancer or neurodegenerative diseases, for example, Alzheimer disease.

The compounds of formula (I) will also inhibit prostanoid-induced smooth muscle contraction and therefore may be used in the treatment of dysmenorrhoea, premature labour, asthma and bronchitis.

The compounds of formula (I) can be used as alternative to conventional non-steroidal anti-inflammatory drugs, particularly where such non-steroidal anti-inflammatory drugs may be contraindicated such as the treatment of patients with gastrointestinal disorders including peptic ulcers, gastritis, regional enteritis, ulcerative colitis, diverticulitis, Crohn's disease, inflammatory bowel syndrome and irritable bowel syndrome, gastrointestinal bleeding and coagulation disorders, kidney disease (e.g. impaired renal function), those prior to surgery or taking anticoagulants, and those susceptible to non-steroidal anti-inflammatory drugs induced asthma.

The compounds can further be used to treat inflammation in diseases such as vascular diseases, migraine headaches, periarteritis nodosa, thyroiditis, aplastic anaemia, Hodgkin's disease, scleroderma, type I diabetes, myasthenia gravis, sarcoidosis, nephrotic syndrome, Behcet's syndrome, polymyositis, hypersensitivity, conjunctivitis, gingivitis and myocardial ischaemia.

Compounds of the present invention are inhibitors of cyclooxygenase-2 enzyme and are thereby useful to treat the cyclooxygenase-2 mediated diseases enumerated above.

Accordingly, the 2-phenylpyran-4-one derivatives of formula (I) and pharmaceutically acceptable salts thereof, and pharmaceutical compositions comprising such compounds and/or salts thereof, may be used in a method of treatment of disorders of the human body which comprises administering to a patient requiring such treatment an effective amount of a 2-phenylpyran-4-one derivative of formula (I) or a pharmaceutically acceptable salt thereof.

The present invention also provides pharmaceutical compositions, which comprise, as an active ingredient, at least a 2-phenylpyran-4-one derivative of formula (I) or a pharmacologically acceptable salt thereof in association with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application.

Preferably the compositions are made up in a form suitable for oral, topical, nasal, inhalation, rectal, percutaneous or injectable administration.

The pharmaceutically acceptable excipients that are admixed with the active compound or salts of such compound, to form the compositions of this invention are well known per se and the actual excipients used depend inter alia on the intended method of administering the compositions.

Compositions of this invention are preferably adapted for injectable and per os administration. In this case, the compositions for oral administration may take the form of tablets, retard tablets, sublingual tablets, capsules or liquid preparations, such as mixtures, elixirs, syrups or suspensions, all containing the compound of the invention; such preparations may be made by methods well-known in the art.

The diluents that may be used in the preparation of the compositions include those liquid and solid diluents that are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 10-600 mg of active ingredient per day. Daily dosage may be administered in one or more treatments, preferably from 1 to 4 treatments, per day.

The invention is illustrated by the following Preparation and Examples, which do not limit the scope of the invention in any way.

Preparation 1

2-(2,4-Difluorophenoxy)-1-(4-methanesulfonylphenyl) ethanone a) To a solution of 2,4-difluorophenol (3.71 g; 29 mmol) and 2-bromo-1-(4-methylsulfanylphenyl)ethanone (7.00 g; 29 mmol) in methylene chloride (50 ml) was added a solution of potassium carbonate (5.91 g; 43 mmol) and tetrabutylammonium hydrogensulfate (0.48 g; 1.4 mmol) in water (20 ml). The mixture was stirred at room temperature for 16 hours. Water (100 ml) was added, the organic phase was decanted, and the basic phase was extracted with methylene chloride (2×100 ml). The organic solution was dried ($Na_2SO_4$) and the solvent removed under reduced pressure. The resulting solid was washed with ethyl ether. 2-(2,4-Difluorophenoxy)-1-(4-methylsulfanyl phenyl)ethanone was obtained (6.60 g, 76%) as an off-white solid.

b) A solution of 80% magnesium monoperoxyphthalate hexahydrate (15.26 g; 25 mmol) in water (20 ml) was added to a solution of the above compound (6.60 g; 22 mmol) in methylene chloride (100 ml). The mixture was stirred at room temperature for 16 hours. The reaction was poured into saturated solution of sodium bicarbonate (200 ml) and extracted with methylene chloride (3×100 ml). The organic phase was dried ($Na_2SO_4$) and the solvent removed under reduced pressure. 2-(2,4-Difluorophenoxy)-1-(4-methanesulfonylphenyl)ethanone was obtained (4.97 g, 89%) as an off-white solid.

δ (DMSO): 3.31 (s, 3H), 5.72 (s, 2H), 6.93-7.05 (m, 1H), 7.15-7.36 (m, 2H), 8.12 (d, J=8.5 Hz, 2H), 8.22 (d, J=8.5 Hz, 2H).

Preparation 2

2-(4-Fluorophenoxy)-1-(4-methanesulfonylphenyl)ethanone

Obtained as an off-white solid (72% overall) from 2-bromo-1-(4-methylsulfanylphenyl)ethanone and 4-fluorophenol by the procedure described in Preparation 1.

δ (DMSO): 3.32 (s, 3H), 5.62 (s, 2H), 7.01-7.04 (m, 2H), 7.05-7.17 (m, 2H), 8.13 (d, J=8.0 Hz, 2H), 8.25 (d, J=8.0 Hz, 2H).

Preparation 3

2-(4-Chlorophenoxy)-1-(4-methanesulfonylphenyl)ethanone

Obtained as an off-white solid (89% overall) from 2-bromo-1-(4-methylsulfanylphenyl)ethanone and 4-chlorophenol by the procedure described in Preparation 1.

δ (DMSO): 3.30 (s, 3H), 5.65 (s, 2H), 7.03 (d, J=8.5 Hz, 2H), 7.32 (d, J=8.5 Hz, 2H), 8.12 (d, J=8.5 Hz, 2H), 8.24 (d, J=8.5 Hz, 2H).

Preparation 4

2-(4-Fluoro-2-methylphenoxy)-1-(4-methanesulfonylphenyl)ethanone

Obtained as an off-white solid (75% overall) from 2-bromo-1-(4-methylsulfanylphenyl)ethanone and 4-fluoro-2-methylphenol by the procedure described in Preparation 1.

δ (DMSO): 2.22 (s, 3H), 3.30 (s, 3H), 5.63 (s, 2H), 6.89-7.06 (m, 3H), 8.08 (d, J=8.0 Hz, 2H), 8.21 (d, J=8.0 Hz, 2H)

Preparation 5

2-(4-Chloro-2-methylphenoxy)-1-(4-methanesulfonylphenyl)ethanone

Obtained as an off-white solid (77% overall) from 2-bromo-1-(4-methylsulfanylphenyl)ethanone and 4-chloro-2-methylphenol by the procedure described in Preparation 1.

δ (DMSO): 2.23 (s, 3H), 3.31 (s, 3H), 5.68 (s, 2H), 6.96 (d, J=8.5 Hz, 1H), 7.15 (d, J=8.5 Hz, 1H), 7.25 (s, 1H), 8.12 (d, J=8.5 Hz, 2H), 8.24 (d, J=8.5 Hz, 2H).

Preparation 6

2-(2-Chloro-4-methylphenoxy)-1-(4-methanesulfonylphenyl)ethanone

Obtained as an off-white solid (84% overall) from 2-bromo-1-(4-methylsulfanylphenyl)ethanone and 2-chloro-4-methylphenol by the procedure described in Preparation 1.

δ (DMSO): 2.23 (s, 1H), 3.32 (s, 3H), 5.74 (s, 2H), 7.02-7.04 (m, 2H), 7.24 (s, H), 8.12 (d, J=8.1 Hz, 2H), 8.22 (d, J=8.1 Hz, 2H).

Preparation 7

2-(2-Bromophenoxy)-1-(4-methanesulfonylphenyl)ethanone

Obtained as an off-white solid (72% overall) from 2-bromo-1-(4-methylsulfanylphenyl)ethanone and 2-bromophenol by the procedure described in Preparation 1.

δ (CDCl$_3$): 3.07 (s, 3H), 5.30 (s, 2H), 6.80-6.94 (m, 2H), 7.20-7.26 (m, 1H), 7.53 (d, J=7.5 Hz, 1H), 8.08 (d, J=9.0 Hz, 2H), 8.23 (d, J=9.0 Hz, 2H).

Preparation 8

2-(3-Bromophenoxy)-1-(4-methanesulfonylphenyl)ethanone

Obtained as an off-white solid (57% overall) from 2-bromo-1-(4-methylsulfanylphenyl)ethanone and 3-bromophenol by the procedure described in Preparation 1.

δ (DMSO): 3.33 (s, 3H), 5.72 (s, 2H), 7.03-7.06 (m, 1H), 7.17 (d, J=8.0 Hz, 1H), 7.25 (d, J=8.0 Hz, 1H), 7.32 (s, 1H), 8.13 (d, J=8.0 Hz, 2H), 8.24 (d, J=8.0 Hz, 2H).

Preparation 9

2-(4-Bromophenoxy)-1-(4-methanesulfonylphenyl)ethanone

Obtained as an off-white solid (81% overall) from 2-bromo-1-(4-methylsulfanylphenyl)ethanone and 4-bromophenol by the procedure described in Preparation 1.

δ (CDCl$_3$): 3.33 (s, 3H), 5.66 (s, 2H), 7.00 (d, J=9.0 Hz, 2H), 7.46 (d, J=9.0 Hz, 2H), 8.12 (d, J=9.0 Hz, 2H), 8.24 (d, J=9.0 Hz, 2H).

Preparation 10

2-(4-Bromo-2-fluorophenoxy)-1-(4-methanesulfonylphenyl)ethanone

Obtained as an off-white solid (78% overall) from 2-bromo-1-(4-methylsulfanylphenyl)ethanone and 4-bromo-2-fluorophenol by the procedure described in Preparation 1.

δ (DMSO): 3.32 (s, 3H), 5.80 (s, 2H), 7.10 (t, J=7.5 Hz, 1H), 7.37 (t, J=7.5 Hz, 1H), 7.60 (d, J=7.5 Hz, 1H), 8.13 (d, J=9.0 Hz, 2H), 8.24 (d, J=9.0 Hz, 2H).

Preparation 11

2-(4-Bromo-2-chlorophenoxy)-1-(4-methanesulfonylphenyl)ethanone

Obtained as an off-white solid (68% overall) from 2-bromo-1-(4-methylsulfanylphenyl)ethanone and 4-bromo-2-chlorophenol by the procedure described in Preparation 1.

δ (CDCl$_3$): 3.13 (s, 3H), 5.32 (s, 2H), 6.77 (d, J=9.0 Hz, 1H), 7.32 (d, J=9.0 Hz, 1H), 7.56 (s, 1H), 8.12 (d, J=7.5 Hz, 2H), 8.24 (d, J=7.5 Hz, 2H).

Preparation 12

2-(2,4-Dibromophenoxy)-1-(4-methanesulfonylphenyl)ethanone

Obtained as an off-white solid (85% overall) from 2-bromo-1-(4-methylsulfanylphenyl)ethanone and 2,4-dibromophenol by the procedure described in Preparation 1.

δ (CDCl$_3$): 3.09 (s, 3H), 5.31 (s, 2H), 6.73 (d, J=9.0 Hz, 1H), 7.36 (d, J=9.0 Hz, 1H), 7.69 (s, 1H), 8.08 (d, J=7.5 Hz, 2H), 8.23 (d, J=7.5 Hz, 2H).

Preparation 13

2-(2,4-Difluorophenoxy)-1-(4-ethanesulfonylphenyl)ethanone

Obtained as an off-white solid (69% overall) from 2-bromo-1-(4-ethylsulfanylphenyl)ethanone and 2,4-difluorophenol by the procedure described in Preparation 1.

δ (CDCl$_3$): 1.31 (t, J=9.0 Hz, 3H), 3.15 (q, J=9.0 Hz, 2H), 5.31 (s, 2H), 6.70-7.03 (m, 3H), 8.03 (d, J=8.0 Hz, 2H), 8.20 (d, J=8.0 Hz, 2H).

Preparation 14

3-(4-Fluorophenoxy)-2-(4-methanesulfonylphenyl)-6-methylpyran-4-one

The title compound of Preparation 2 (0.75 g, 2.43 mmol) was added to a suspension of polyphosphoric acid (7.5 g) in acetic acid (11 ml), pre-heated at 95-100° C. The mixture was heated at 140° C. for 4 hours. After cooling, the reaction was poured into ice-water, extracted with ethyl acetate (2×100 ml), the organic solution dried (Na$_2$SO$_4$), and the solvent removed under reduced pressure. The residual oil was purified by column chromatography with silica gel and ethyl acetate/n-hexane (1:1) as eluent. 3-(4-Fluorophenoxy)-

2-(4-methanesulfonylphenyl)-6-methylpyran-4-one was obtained (0.26 g, 11%) as an off-white solid.

δ (DMSO): 2.40 (s, 3H), 3.27 (s, 3H), 6.42 (s, 1H), 6.94-7.04 (m, 2H), 7.06-7.14 (m, 2H), 8.04 (s, 4H).

Preparation 15

3-(4-Bromophenoxy)-2-(4-methanesulfonylphenyl)-6-methylpyran-4-one

Obtained as an off-white solid (19%) from the tittle compound of Preparation 9 and acetic acid by the procedure described in Preparation 14.

δ (CDCl$_3$): 2.44 (s, 3H), 3.06 (s, 3H), 6.36 (s, 1H) 6.89 (d, J=9.0 Hz, 2H), 7.20 (d, J=9.0 Hz, 2H), 8.00 (d, J=9.0 Hz, 2H), 8.07 (d, J=9.0 Hz, 2H).

Preparation 16

Acetic acid 2-(2,4-difluorophenoxy)-1(4-methanesulfonylphenyl)vinyl ester

Methanesulfonic acid (7.41 g, 77 mmol) was added to a mixture of the title compound of Preparation 1 (10.0 g, 30.7 mmol) and acetic anhydride (20.0 g, 0.196 mol), pre-heated at 80° C. After 2 hours, the reaction was cooled and water (50 ml) was added slowly, maintaining the temperature below 30° C. The mixture was stirred for 30 minutes. The resulting solid was washed with water and dried at 45° C. under reduced pressure. Acetic acid 2-(2,4-difluorophenoxy)-1-(4-methanesulfonylphenyl)vinyl ester was obtained (10.2 g, 90%) as a white solid.

δ (DMSO): 2.33 (s, 3H), 3.20 (s, 3H), 7.08-7.16 (m, 1H), 7.40-7.57 (m, 2H), 7.77 (d, J=8.7 Hz, 2H), 7.88 (d, J=8.7 Hz, 2H), 7.89 (s, 1H).

Preparation 17

Acetic acid 2-(4-chlorophenoxy)-1-(4-methanesulfonylphenyl)vinyl ester

Obtained as an off-white solid (49%) from the title compound of Preparation 3 and acetic anhydride by the procedure described in Preparation 16.

δ (DMSO): 2.37 (s, 3H), 3.24 (s, 3H), 7.29 (d, J=9.0 Hz, 2H), 7.47 (d, J=9.0 Hz, 2H), 7.82 (d, J=8.7 Hz, 2H), 7.91 (d, J=8.7 Hz, 2H), 7.94 (s, 1H).

Preparation 18

Propionic acid 2-(2,4-difluorophenoxy)-1-(4-methanesulfonylphenyl)vinyl ester

Obtained as a white solid (55%) from the title compound of Preparation 1 and propionic anhydride by the procedure described in Preparation 16.

δ (CDCl$_3$): 1.31 (t, J=7.5 Hz, 3H), 2.69 (q, J=7.5 HZ, 2H) 6.87-6.97 (m, 2H), 7.04 (s, 1H), 7.14-7.24 (m, 1H), 7.56 (d, J=8.0 Hz, 2H), 7.92 (d, J=8.0 Hz, 2H).

Preparation 19

3-(2,4-Difluorophenoxy)-2-(4-methanesulfonylphenyl)-6-methylpyran-4-one

The title compound of Preparation 16 (10.0 g, 27 mmol) was added to a solution of polyphosphoric acid (75 g) in acetic anhydride (10.0 g, 98 mmol), pre-heated at 95-100° C. After 40 minutes, the reaction was cooled at 40-50° C. Methanol/water (1:2) (113 ml) was added, maintaining the temperature below 80° C., and the mixture was stirred 16 hours. The resulting solid was filtered and refluxed in methanol (45 ml) for 2 hours. After cooling, the solid was filtered and recrystallized from methylethylketone, to give 3-(2,4-difluorophenoxy)-2-(4-methanesulfonylphenyl)-6-methylpyran-4-one (3.86 g, 36%) as an off-white solid.

δ (DMSO): 2.44 (s, 3H), 3.26 (s, 3H), 6.48 (s, 1H), 6.89-6.98 (m, 1H), 7.04-7.14 (m, 1H), 7.34-7.44 (m, 1H), 8.09 (s, 4H).

Preparation 20

3-(4-Chlorophenoxy)-2-(4-methanesulfonylphenyl)-6-methylpyran-4-one

Obtained from the title compound of Preparation 17 and acetic anhydride by the procedure described in Preparation 19. Purification by column chromatography with silica gel and ethyl acetate/n-hexane (3:2) as eluent gave 3-(4-chlorophenoxy)-2-(4-methanesulfonylphenyl)-6-methylpyran-4-one (32%) as an off-white solid.

δ (DMSO): 2.44 (s, 3H), 3.26 (s, 3H), 6.48 (s, 1H), 7.20 (d, J=9.0 Hz, 2H), 7.34 (d, J=9.0 Hz, 2H), 8.06 (s, 4H).

Preparation 21

5-(2,4-Difluorophenoxy)-6-(4-methanesulfonylphenyl)-4-oxo-4H-pyran-2-carbaldehyde Selenium dioxide (7.0 g, 63 mmol) was added to a solution of the title compound of Preparation 19 (5.0 g, 12.7 mmol) in dioxane (55 ml), and the mixture was heated into a sealed tube at 180° C. for 60 minutes. After cooling, the crude material was filtered through Celite® and the solvent was removed under reduced pressure. The resulting oil was purified by column chromatography with silica gel and ethyl acetate/n-hexane (2:1) as eluent. 5-(2,4-Difluorophenoxy)-6-(4-methanesulfonylphenyl)-4-oxo-4H-pyran-2-carbaldehyde (2.93 g, 57%) was obtained as an off-white solid.

δ (CDCl$_3$): 3.09 (s, 3H), 6.72-6.83 (m, 1H), 6.88-6.96 (m, 2H), 7.11 (s, 1H), 8.11 (d, J=8.0 Hz, 2H), 8.27 (d, J=8.0 Hz, 2H), 9.80 (s, 1H).

Preparation 22

5-(4-Fluorophenoxy)-6-(4-methanesulfonylphenyl)-4-oxo-4H-pyran-2-carbaldehyde

Obtained as a brown oil (70% purity, used in the next step without further purification) from the title compound of Preparation 14 by the procedure described in Preparation 21.

δ (CDCl$_3$): 3.09 (s, 3H), 6.90-6.98 (m, 4H), 7.01 (s, 1H), 8.07 (d, J=8.5 Hz, 2H), 8.22 (d, J=8.5 Hz, 2H), 9.82 (s, 1H).

Preparation 23

5-(4-Chlorophenoxy)-6-(4-methanesulfonylphenyl)-4-oxo-4H-pyran-2-carbaldehyde

Obtained as a brown oil (70% purity, used in the next step without further purification) from the title compound of Preparation 20 by the procedure described in Preparation 21.

δ (CDCl$_3$): 3.09 (s, 3H), 6.91 (d, J=8.0 Hz, 2H), 7.15 (s, 1H), 7.29 (d, J=8.0 Hz, 2H), 8.07 (d, J=8.0 Hz, 2H), 8.10 (d, J=8.0 Hz, 2H), 9.83 (s, 1H).

Preparation 24

5-(4-Bromophenoxy)-6-(4-methanesulfonylphenyl)-4-oxo-4H-pyran-2-carbaldehyde

Obtained as a brown oil (80% purity, used in the next step without further purification) from the title compound of Preparation 15 by the procedure described in Preparation 21.

δ (CDCl$_3$): 3.71 (s, 3H), 6.92 (d, J=9.0 Hz, 2H), 7.16 (s, 1H), 7.44 (d, J=9.0 Hz, 2H), 8.05 (d, J=9.0 Hz, 2H), 8.20 (d, J=9.0 Hz, 2H), 9.80(s, 1H).

Preparation 25

5-(2-Fluoro-4-bromophenoxy)-6-(4-methanesulfonylphenyl)-4-oxo-4H-pyran-2-carbaldehyde Obtained as a brown oil (65% purity, used in the next step without further purification) from the title compound of Example 6 by the procedure described in Preparation 21.

δ (CDCl$_3$): 3.09 (s, 3H), 6.80 (t, J=12.0 Hz, 1H), 7.08-7.20 (m, 1H), 7.11 (s, 1H), 7.25-7.36 (m, 1H), 8.09 (d, J=9.0 Hz, 2H), 8.22 (d, J=9.0 Hz, 2H), 9.80 (s, 1H).

EXAMPLE 1

3-(4-Fluoro-2-methylphenoxy)-2-(4-methanesulfonylphenyl)-6-methyl pyran-4-one

The title compound of Preparation 4 (11.15 g, 35 mmol) was added to a solution of polyphosphoric acid (115 g) in acetic anhydride (48.7 g, 0.48 mol), pre-heated at 95-100° C. The mixture was heated at the same temperature for 1.5 hours. After cooling, the reaction was poured into ice-water, extracted with ethyl acetate (3×200 ml), the organic solution dried (Na$_2$SO$_4$), and the solvent removed under reduced pressure. The residual oil was purified by column chromatography with silica gel and ethyl acetate/n-hexane (3:1) as eluent. 3-(4-Fluoro-2-methylphenoxy)-2-(4-methanesulfonylphenyl)-6-methylpyran-4-one (2.29 g, 17%) was obtained as an off-white solid.

m.p.: 146° C.

δ (DMSO): 2.32 (s, 3H), 2.43 (s, 3H), 3.27 (s, 3H), 6.46 (s, 1H), 6.69-6.72 (m, 1H), 6.83-6.86 (m, 1H), 7.10-7.13 (m, 1H), 8.09 (s, 4H).

EXAMPLE 2

3-(4-Chloro-2-methylphenoxy)-2-(4-methanesulfonylphenyl)-6-methyl pyran-4-one

Obtained as an off-white solid (15%) from the title compound of Preparation 5 and acetic anhydride by the procedure described in Example 1.

m.p.: 198° C.

δ (DMSO): 2.31 (s, 3H), 2.44 (s, 3H), 3.27 (s, 3H), 6.47 (s, 1H), 6.72 (d, J=9.0 Hz, 1H), 7.07 (d, J=9.0 Hz, 1H), 7.32 (s, 1H), 8.08 (s, 4H).

EXAMPLE 3

3-(2-Chloro-4-methylphenoxy)-2-(4-methanesulfonylphenyl)-6-methyl pyran-4-one

Obtained as an off-white solid (28%) from the title compound of Preparation 6 and acetic anhydride by the procedure described in Example 1.

m.p.: 159° C.

δ (DMSO): 2.23 (s, 3H), 2.44 (s, 3H), 3.27 (s, 3H), 6.48 (s, 1H), 6.81 (d, J=8.7 Hz, 1H), 6.98 (d, J=8.7 Hz, 1H), 7.32 (s, 1H), 8.07 (s, 4H).

EXAMPLE 4

3-(2-Bromophenoxy)-2-(4-methanesulfonylphenyl)-6-methylpyran-4-one

Obtained as an off-white solid (32%) from the title compound of Preparation 7 and acetic anhydride by the procedure described in Example 1.

m.p.: 197-199° C.

δ (CDCl$_3$): 2.46 (s, 3H), 3.11 (s, 3H), 6.43 (s, 1H), 6.67 (d, J=7.5 Hz, 1H), 6.92 (t, J=7.5 Hz, 1H), 7.18 (t, J=7.5 Hz, 1H), 7.62 (t, J=7.5 Hz, 1H), 8.04 (d, J=9.0 Hz, 2H), 8.18 (d, J=9.0 Hz, 2H).

EXAMPLE 5

3-(3-Bromophenoxy)-2-(4-methanesulfonylphenyl)-6-methylpyran-4-one

Obtained as an off-white solid (15%) from the title compound of Preparation 8 and acetic anhydride by the procedure described in Example 1.

LRMS: m/z 434 (M+1)$^+$.

δ (CDCl$_3$): 2.45 (s, 3H), 3.09 (s, 3H), 6.40 (s, 1H), 6.91-6.93 (m, 1H), 7.08 (s, 1H), 7.15-7.20 (m, 2H), 8.03 (d, J=8.5 Hz, 2H), 8.07 (d, J=8.5 Hz, 2H).

EXAMPLE 6

3-(4-Bromo-2-fluorophenoxy)-2-(4-methanesulfonylphenyl)-6-methyl pyran-4-one

Obtained as an off-white solid (31%) from the title compound of Preparation 10 and acetic anhydride by the procedure described in Example 1.

m.p.: 215° C.

δ (CDCl$_3$): 2.45 (s, 3H), 3.08 (s, 3H), 6.34 (s, 1H), 6.74 (t, J=9.0 Hz, 1H), 7.12 (d, J=9.0 Hz, 1H), 7.29 (d, J=9.0 Hz, 1H), 8.04 (d, J=9.0 Hz, 2H), 8.10 (d, J=9.0 Hz, 2H).

EXAMPLE 7

3-(4-Bromo-2-chlorophenoxy)-2-(4-methanesulfonylphenyl)-6-methyl pyran-4-one

Obtained as an off-white solid (43%) from the title compound of Preparation 11 and acetic anhydride by the procedure described in Example 1.

m.p.: 214-215° C.

δ (CDCl$_3$): 2.47 (s, 3H), 3.08 (s, 3H), 6.37 (S, 1H), 6.58 (d, J=8.5 Hz, 1H), 7.20 (d, J=8.5 Hz, 1H), 7.56 (s, 1H), 8.03 (d, J=7.5 Hz, 2H), 8.12 (d, J=7.5 Hz, 2H).

EXAMPLE 8

3-(2,4-Dibromophenoxy)-2-(4-methanesulfonylphenyl)-6-methyl-pyran-4-one

Obtained as an off-white solid (17%) from the title compound of Preparation 12 and acetic anhydride by the procedure described in Example 1.

m.p.: 231° C.

δ (CDCl$_3$): 2.46 (s, 3H), 3.08 (s, 3H), 6.37 (s, 1H), 6.55 (d, J=9.0 Hz, 1H), 7.25 (d, J=9.0 Hz, 1H), 7.73 (s, 1H), 8.03 (d, J=7.5 Hz, 2H), 8.13 (d, J=7.5 Hz, 2H).

EXAMPLE 9

3-(2,4-Difluorophenoxy)-2-(4-ethanesulfonylphenyl)-6-methyl-pyran-4-one

Obtained as an off-white solid (18%) from the title compound of Preparation 13 and acetic anhydride by the procedure described in Example 1.

m.p.: 154-155° C.

δ (CDCl₃): 1.30 (t, J=7.5 Hz, 3H), 2.45 (s, 3H), 3.15 (q, J=7.5 Hz, 2H), 6.33 (s, 1H), 6.69-6.76 (m, 1H), 6.81-6.93 (m, 2H), 8.00 (d, J=8.7 Hz, 2H), 8.12 (d, J=8.7 Hz, 2H)

EXAMPLE 10

2-(4-Methanesulfonylphenyl)-6-methyl-3-(2-methylphenoxy)pyran-4-one

To a solution of the title compound of Example 4 (1.40 g, 3.21 mmol) in dimethylformamide (16 ml) were added tetramethyltin (2.40 ml, 17.3 mmol), tri-o-tolylphosphine (0.23 g, 0.77 mmol), palladium acetate (0.043 g, 0.19 mmol) and triethylamine (1.45 ml, 10.3 mmol). The mixture was heated at 105° C. for 90 hours. After cooling, the crude material was filtered through Celite® and the solvent was removed under reduced pressure. The resulting oil was dissolved in ethyl acetate (50 ml). The organic solution was washed with water (2×50 ml), dried (Na₂SO₄), and the solvent removed under reduced pressure. The resulting oil was purified by column chromatography with silica gel and ethyl acetate/n-hexane (2:1) as eluent. 2-(4-Methanesulfonylphenyl)-6-methyl-3-(2-methylphenoxy)pyran-4-one (0.77 g, 65%) was obtained as an off-white solid.

m.p.: 168° C.

δ (DMSO): 2.32 (s, 3H), 2.44 (s, 3H), 3.26 (s, 3H), 6.46 (s, 1H), 6.65 (d, J=7.5 Hz, 1H), 6.89-6.94 (m, 1H), 6.99-7.02 (m, 1H), 7.22 (d, J=7.5 Hz, 1H), 8.06 (d, J=9.0 Hz, 2H), 8.11 (d, J=9.0 Hz, 2H).

EXAMPLE 11

2-(4-Methanesulfonylphenyl)-6-methyl-3-(3-methylphenoxy)pyran-4-one

Obtained from the title compound of Example 5 by the procedure described in Example 10. Recrystallization from ethanol/water (1:2) gave 2-(4-methanesulfonylphenyl)-6-methyl-3-(3-methylphenoxy)pyran-4-one (0.28 g, 29%) as an off-white solid.

m.p.: 162° C.

δ (DMSO): 2.25 (s, 3H), 2.44 (s, 3H), 3.26 (s, 3H), 6.46 (s, 1H), 6.73-6.85 (m, 3H), 7.13-7.19 (m, 1H), 8.07 (s, 4H).

EXAMPLE 12

3-(2-Fluoro-4-methylphenoxy)-2-(4-methanesulfonylphenyl)-6-methyl pyran-4-one

Obtained from the title compound of Example 6 by the procedure described in Example 10. Purification by column chromatography with silica gel and ethyl acetate/n-hexane (3:2) as eluent gave 3-(2-fluoro-4-methylphenoxy)-2-(4-methanesulfonylphenyl)-6-methylpyran-4-one (64%) as a white solid.

m.p.: 171° C.

δ (DMSO): 2.24 (s, 3H), 2.43 (s, 3H), 3.27 (s, 3H), 6.47 (s, 1H), 6.83-6.90 (m, 2H), 7.12 (d, J=12.0 Hz, 1H), 8.08 (s, 4H).

EXAMPLE 13

3-(2,4-Difluorophenoxy)-6-ethyl-2-(4-methanesulfonylphenyl)-5-methyl pyran-4-one Obtained from the title compound of Preparation 18 and propionic anhydride by the procedure described in Preparation 19. Purification by column chromatography with silica gel and ethyl acetate/n-hexane (1:2) as eluent gave 3-(2,4-difluorophenoxy)-6-ethyl-2-(4-methane sulfonylphenyl)-5-methylpyran-4-one (21%) as an off-white solid.

m.p.: 200° C.

δ (DMSO): 1.29 (t, J=7.5 Hz, 3H), 1.92 (s, 3H), 2.81 (q, J=7.5 Hz, 2H), 3.27 (s, 3H), 6.90-6.96 (m, 1H), 7.02-7.08 (m, 1H), 7.37-7.44 (m, 1H), 8.10 (s, 4H).

EXAMPLE 14

3-Chloro-5-(2,4-difluorophenoxy)-6-(4-methanesulfonylphenyl)-2-methyl pyran-4-one To a solution of the title compound of Preparation 19 (0.5 g, 1.28 mmol) in dry pyridine (10 ml), was added sulfuryl chloride (0.21 ml, 2.56 mmol) dropwise. The mixture was stirred at room temperature overnight. The crude reaction was poured into ice/2 N hydrochloric acid (75 ml) and extracted with ethyl acetate (2×100 ml). The organic phase was washed with water (2×50 ml) and dried (Na₂SO₄). The solvent was removed under reduced pressure and the residue was purified by column chromatography with silica gel and ethyl acetate/n-hexane (1:2) as eluent. 3-Chloro-5-(2,4-difluorophenoxy)-6-(4-methanesulfonylphenyl)-2-methylpyran-4-one (0.22 g, 40%) was obtained as a white solid.

m.p.: 210° C.

δ (DMSO): 2.62 (s, 3H), 3.28 (s, 3H), 6.93-6.99 (m, 1H), 7.17-7.22 (m, 1H), 7.39-7.46 (m, 1H), 8.06-8.10 (m, 4H).

EXAMPLE 15

3-Chloro-5-(4-fluorophenoxy)-6-(4-methanesulfonylphenyl)-2-methyl pyran-4-one

Obtained from the title compound of Preparation 14 by the procedure described in Example 14. Purification by column chromatography with silica gel and methylene chloride/ethyl acetate (9:1) as eluent gave 3-chloro-5-(4-fluorophenoxy)-6-(4-methanesulfonylphenyl)-2-methylpyran-4-one (20%) as an off-white solid.

m.p.: 279° C.

δ (DMSO): 2.62 (s, 3H), 3.27 (s, 3H), 7.05-7.17 (m, 4H), 8.08 (s, 4H).

EXAMPLE 16

3-Chloro-5-(4-chlorophenoxy)-6-(4-methanesulfonylphenyl)-2-methyl pyran-4-one

Obtained from the title compound of Preparation 20 by the procedure described in Example 14. Recrystallization from ethanol gave 3-chloro-5-(4-chlorophenoxy)-6-(4-methanesulfonylphenyl)-2-methylpyran-4-one (45%) as a white solid.

m.p.: 274° C.

δ (DMSO): 2.62 (s, 3H), 3.27 (s, 3H), 7.09 (d, J=6.7 Hz, 2H), 7.36 (d, J=6.7 Hz, 2H), 8.07 (s, 4H).

EXAMPLE 17

3-Bromo-5-(2,4-difluorophenoxy)-6-(4-methanesulfonylphenyl)-2-methyl pyran-4-one To a solution of the title compound of Preparation 19 (5.0 g, 12.7 mmol) in chloroform (100 ml), were added pyridine (1.10 g, 14.0 mmol) and pyridinium tribromide (10.0 g, 28.0 mmol). The mixture was stirred at room temperature for 30 minutes and then refluxed for 92 hours. The crude reaction was diluted with chloroform (100 ml), washed with 2 N hydrochloric acid (2×75 ml) and water (2×75 ml), and dried ($Na_2SO_4$). The solvent was removed under reduced pressure and the residue was purified by column chromatography with silica gel and ethyl acetate/n-hexane (1:1) as eluent. 3-Bromo-5-(2,4-difluoro phenoxy)-6-(4-methanesulfonylphenyl)-6-methylpyran-4-one (1.10 g, 18%) was obtained as a white solid.

m.p.: 230° C.

δ (DMSO): 2.67 (s, 3H), 3.28 (s, 3H), 6.92-6.99 (m, 1H), 7.12-7.19 (m, 1H), 7.38-7.46 (m, 1H), 8.07 (s, 4H).

EXAMPLE 18

3-Bromo-5-(4-chlorophenoxy)-6-(4-methanesulfonylphenyl)-2-methyl pyran-4-one

Obtained from the title compound of Preparation 20 by the procedure described in Example 17. Purification by column chromatography with silica gel and ethyl acetate/n-hexane (2:1) as eluent gave 3-bromo-5-(4-chlorophenoxy)-6-(4-methanesulfonylphenyl)-2-methylpyran-4-one (10%) as an off-white solid.

m.p.: 251° C.

δ (DMSO): 2.67 (s, 3H), 3.27 (s, 3H), 7.08 (d, J=9.0 Hz, 2H), 7.35 (d, J=9.0 Hz, 2H), 8.07 (s, 4H).

EXAMPLE 19

3-(2,4-Difluorophenoxy)-5,6-dimethyl-2-(4-methanesulfonylphenyl)pyran-4-one

To a solution of the title compound of Example 17 (0.50 g, 1.1 mmol) in dimethylformamide (10 ml) were added tetramethyltin (0.87 ml, 6.3 mmol), tri-o-tolylphosphine (0.20 g, 0.68 mmol), palladium acetate (0.038 g, 0.17 mmol) and triethylamine (0.30 ml, 2.2 mmol). The mixture was heated at 100° C. for 120 hours. After cooling, the crude material was filtered through Celite® and the solvent was removed under reduced pressure. The resulting oil was dissolved in ethyl acetate (50 ml). The organic solution was washed with 2 N hydrochloric acid (2×50 ml) and water (2×50 ml), dried ($Na_2SO_4$), and the solvent removed under reduced pressure. The resulting residue was purified by crystallization from isopropyl ether. 3-(2,4-Difluorophenoxy)-5,6-dimethyl-2-(4-methanesulfonylphenyl)pyran-4-one (0.25 g, 58%) as an off-white solid.

m.p.: 192° C.

δ (DMSO): 1.90 (s, 3H), 2.47 (s, 3H), 3.27 (s, 3H), 6.89-6.94 (m, 1H), 7.00-7.08 (m, 1H), 7.37-7.43 (m, 1H), 8.09 (s, 4H).

EXAMPLE 20

3-(2,4-Difluorophenoxy)-2-(4-methanesulfonylphenyl)-6-methyl-5-vinyl pyran-4-one To a solution of the title compound of Example 17 (0.50 g, 1.1 mmol) in dimethylformamide (10 ml) were added tributylvinyltin (1.24 ml, 4.24 mmol), tri-o-tolylphosphine (0.10 g, 0.34 mmol), palladium acetate (0.019 g, 0.084 mmol) and triethylamine (0.15 ml, 1.1 mmol). The mixture was heated at 100° C. overnight. After cooling, the crude material was filtered through Celitee and diluted with ethyl acetate (50 ml). The organic solution was washed with 2 N hydrochloric acid (2×50 ml) and water (2×50 ml), dried ($Na_2SO_4$), and the solvent removed under reduced pressure. The resulting residue was purified by column chromatography with silica gel and ethyl acetate/n-hexane (2:3) as eluent. 3-(2,4-Difluorophenoxy)-2-(4-methanesulfonylphenyl)-6-methyl-5-vinylpyran-4-one (0.25 g, 57%) was obtained as a white solid.

m.p.: 184° C.

δ (DMSO): 2.58 (s, 3H), 3.27 (s, 3H), 5.50 (dd, J=2.4 Hz, J=12.0 Hz, 1H), 6.24 (dd, J=2.4 Hz, J=17.7 Hz, 1H), 6.54 (dd, J=12.0 Hz, J=17.7 Hz, 1H), 6.90-6.96 (m, 1H), 7.10-7.15 (m, 1H), 7.34-7.43 (m, 1H), 8.07-8.13 (m, 4H).

EXAMPLE 21

3-(2,4-Difluorophenoxy)-5-ethyl-2-(4-methanesulfonylphenyl)-6-methyl pyran-4-one To a solution of the title compound of Example 20 (0.14 g, 0.33 mmol) in ethyl acetate (25 ml) and methanol (50 ml) was added palladium on charcoal (14 mg, 10%). The mixture was hydrogenated at room temperature and at 30 psi for 1 hour. The crude material was filtered through Celite® and the solvent was removed under reduced pressure. The resulting residue was purified by column chromatography with silica gel and ethyl acetate/n-hexane (2:3) as eluent. 3-(2,4-Difluorophenoxy)-5-ethyl-2-(4-methanesulfonylphenyl)-6-methylpyran-4-one (0.063 g, 45%) was obtained as an off-white solid.

m.p.: 173° C.

δ ($CDCl_3$): 1.09 (t, J=7.5 Hz, 3H), 2.47 (s, 3H), 2.49 (q, J=7.5 Hz, 2H), 3.09 (s, 3H), 6.72-6.75 (m, 1H), 6.81-6.91 (m, 2H), 8.03 (d, J=8.5 Hz, 2H), 8.14 (d, J=8.5 Hz, 2H).

EXAMPLE 22

3-(2,4-Difluorophenoxy)-6-hydroxymethyl-2-(4-methanesulfonylphenyl) pyran-4-one

To a solution of the title compound of Preparation 21 (1.36 g, 3.3 mmol) in methanol (20 ml), sodium borohydride (0.19 g, 5.2 mmol) was slowly added at 0° C. The resulting mixture was stirred for 30 minutes at room temperature. The reaction mixture was concentrated and the residue was dissolved in ethyl acetate. The organic layer was washed with water, dried ($Na_2SO_4$), and the solvent was removed under reduced pressure. The resulting residue was purified by column chromatography with silica gel and ethyl acetate/n-hexane (2:1) as eluent. 3-(2,4-Difluorophenoxy)-6-hydroxymethyl-2-(4-methanesulfonylphenyl)pyran-4-one (0.65 g, 48%) was obtained as a white solid.

m.p.: 205° C.

δ (DMSO): 3.27 (s, 3H), 4.50 (d, J=6.0 Hz, 2H), 5.90 (t, J=6.0 Hz, 1H), 6.52 (s, 1H), 6.61-6.67 (m, 1H), 7.07-7.14 (m, 1H), 7.37-7.43 (m, 1H), 8.09 (s, 4H).

EXAMPLE 23

3-(4-Fluorophenoxy)-6-hydroxymethyl-2-(4-methanesulfonylphenyl)pyran-4-one

Obtained from the title compound of Preparation 22 by the procedure described in Example 22. Recrystallization from ethanol gave 3-(4-fluorophenoxy)-6-hydroxymethyl-2-(4-methanesulfonylphenyl)pyran-4-one (30%) as an off-white solid.

m.p.: 206° C.

δ (DMSO): 3.27 (s, 3H), 4.50 (d, J=6.0 Hz, 2H), 5.91 (t, J=6.0 Hz, 1H), 6.52 (s, 1H), 6.98-7.04 (m, 2H), 7.10-7.16 (m, 2H), 8.06 (d, J=8.0 Hz, 2H), 8.10 (d, J=8.0 Hz, 2H).

EXAMPLE 24

3-(4-Chlorophenoxy)-6-hydroxymethyl-2-(4-methanesulfonylphenyl)pyran-4-one

Obtained from the title compound of Preparation 23 by the procedure described in Example 22. Recrystallization from ethanol gave 3-(4-chlorophenoxy)-6-hydroxymethyl-2-(4-methanesulfonylphenyl)pyran-4-one (49%) as an off-white solid.

m.p.: 227° C.

δ (DMSO): 3.26 (s, 3H), 4.50 (d, J=6.0 Hz, 2H), 5.91 (t, J=60 Hz, 1H), 6.53 (s, 1H), 7.04 (d, J=7.0 Hz, 2H), 7.34 (d, J=7.0 Hz, 2H), 8.07 (s, 4H).

EXAMPLE 25

3-(2-Fluoro-4-bromophenoxy)-6-hydroxymethyl-2-(4-methanesulfonyl phenyl)pyran-4-one Obtained from the title compound of Preparation 24 by the procedure described in Example 22 Purification by column chromatography with silica gel and ethyl acetate gave 3-(2-fluoro-4-bromophenoxy)-6-hydroxymethyl-2-(4-methanesulfonylphenyl)pyran-4-one (34%) as an off-white solid.

m.p.: 202-203° C.

δ (CDCl$_3$):3.08 (s, 3H), 4.64 (s, 2H), 6.62 (s, 1H), 6.74 (t, J=8.9 Hz, 1H), 7.12 (dd, J=1.5 Hz, J=8.9 Hz, 1H), 7.29 (dd, J=2.4 Hz, J=10.5, 1H), 8.02 (d, J=8.9 Hz, 2H), 8.08 (d, J=8.9 Hz, 2H).

EXAMPLE 26

3-(2,4-Difluorophenoxy)-2-(4-methanesulfonylphenyl)-6-methoxymethyl pyran-4-one

To a solution of the title compound of Example 22 (0.64 g, 1.6 mmol) in methylene chloride (30 ml) and tetrahydrofuran (20 ml) were added methyl iodide (0.29 ml, 4.7 mmol) and a solution of sodium hydroxide (0.50 g, 12.5 mmol) and tetrabutylammonium chloride (50 mg) in water (1 ml). The reaction mixture was stirred at room temperature for 18 hours. The organic layer was diluted with methylene chloride (30 ml), washed with water, dried (Na$_2$SO$_4$), and the solvent was removed under reduced pressure. The resulting solid was purified by column chromatography with silica gel and methylene chloride/ethyl acetate/acetic acid (78:10:1) as eluent. 3-(2,4-Difluorophenoxy)-2-(4-methanesulfonylphenyl)-6-methoxymethylpyran-4-one (0.09 g, 14%) was obtained as an off white solid.

m.p.: 124° C.

δ (DMSO): 3.27 (s, 3H), 3.43 (s, 3H), 4.47 (s, 2H), 6.57 (s, 1H), 6.70-6.94 (m, 1H), 7.10-7.18 (m, 1H), 7.39-7.43 (m, 1H), 8.06 (d, J=9.0 Hz, 2H), 8.11 (d, J=9.0 Hz, 2H).

EXAMPLE 27

3-(4-Fluorophenoxy)-2-(4-methanesulfonylphenyl)-6-methoxymethylpyran-4-one

To a solution of the title compound of Example 23 (0.74 g, 0.9 mmol) in methanol (50 ml) were added methyl iodide (0.36 ml, 5.8 mmol) and freshly prepared silver oxide (1.75 g, 7.59 mmol). The reaction mixture was stirred at room temperature for 18 hours. The crude material was filtered through Celite® and washed with methanol (3×25 ml). The organic solution was washed with diluted ammonium hydroxide (2×50 ml) and water (2×50 ml), dried (Na$_2$SO$_4$), and the solvent removed under reduced pressure. The resulting residue was purified by column chromatography with silica gel and methylene chloride/ethyl acetate/acetic acid (78:10:1) as eluent. 3-(4-Fluorophenoxy)-2-(4-methanesulfonylphenyl)-6-methoxymethylpyran-4-one (0.40 g, 52%) was obtained as a white solid.

m.p.: 165° C.

δ (DMSO): 3.27 (s, 3H), 3.43 (s, 3H), 4.48 (s, 2H), 6.57 (s, 1H), 7.05-7.13 (m, 4H), 8.07 (s, 4H).

EXAMPLE 28

3-(4-Chlorophenoxy)-2-(4-methanesulfonylphenyl)-6-methoxymethylpyran-4-one

Obtained from the title compound of Example 24 by the procedure described in Example 27. Purification by column chromatography with silica gel and methylene chloride/ethanol/ammonium hydroxide (100:8:1) as eluent gave 3-(4-chlorophenoxy)-2-(4-methanesulfonylphenyl)-6-methoxymethylpyran-4-one (49%) as an off-white solid.

m.p.: 156° C.

δ (DMSO): 3.26 (s, 3H), 3.42 (s, 3H), 4.47 (s, 2H), 6.58 (s, 1H), 7.05 (d, J=7.5 Hz, 2H), 7.35 (d, J=7.5 Hz, 2H), 8.04 (d, J=9.0 Hz, 2H), 8.08 (d, J=9.0 Hz, 2H).

EXAMPLE 29

Acetic acid [5-(2,4-difluorophenoxy)-6-(4-methanesulfonylphenyl)-4-oxo-4H-pyran-2-yl]methyl ester To a solution of the title compound of Example 22 (0.75 g, 1.8 mmol) in methylene chloride (10 ml) were added triethyl amine (0.28 ml, 2.0 mmol) and acetyl chloride (0.14 ml, 2.02 mmol). The mixture was stirred at room temperature for 4 hours. The crude material was poured into ice and diluted with methylene chloride (50 ml). The organic solution was washed with sodium bicarbonate (4%, 2×50 ml) and water (2×50 ml), dried (Na$_2$SO$_4$), and the solvent removed under reduced pressure. The resulting residue was purified by column chromatography with silica gel and ethyl acetate/n-hexane (2:1) as eluent. Acetic acid [5-(2,4-difluorophenoxy)-6-(4-methanesulfonyl phenyl)-4-oxo-4H-pyran-2-yl] methyl ester (0.39 g, 47%) was obtained as a white solid.

m.p.: 175° C.

δ (DMSO): 2.17 (s, 3H), 3.28 (s, 3H), 5.14 (s, 2H), 6.68 (s, 1H), 6.94-6.97 (m, 1H), 7.09-7.16 (m, 1H), 7.36-7.44 (m, 1H), 8.06-8.12 (m, 4H)

EXAMPLE 30

Acetic acid [5-(4-fluorophenoxy)-6-(4-methanesulfonylphenyl)-4-oxo-4H-pyran-2-yl]methyl ester Obtained from the title compound of Example 23 by the procedure described in Example 29. Purification by column chromatography with silica gel and ethyl acetate/n-hexane (3:2) as eluent gave acetic acid [5-(4-fluorophenoxy)-6-(4-methanesulfonylphenyl)-4-oxo-4H-pyran-2-yl]methyl ester (47%) as an off-white solid.

m.p.: 180° C.

δ (DMSO): 2.17 (s, 3H), 3.27 (s, 3H), 5.14 (s, 2H), 6.69 (s, 1H), 7.01-7.06 (m, 2H), 7.10-7.16 (m, 2H), 8.08 (s, 4H).

EXAMPLE 31

Acetic acid [5-(4-chlorophenoxy)-6-(4-methanesulfonylphenyl)-4-oxo-4H-pyran-2-yl]methyl ester Obtained from the title compound of Example 24 by the procedure described in Example 29. Purification by column chromatography with silica gel and ethyl acetate/n-hexane (1:1) as eluent gave acetic acid [5-(4-chlorophenoxy)-6-(4-methanesulfonylphenyl)-4-oxo-4H-pyran-2-yl]methyl ester (47%) as an off-white solid.

m.p.: 115° C.

δ (DMSO): 2.17 (s, 3H), 3.27 (s, 3H), 5.15 (s, 2H), 6.69 (s, 1H), 7.05 (d, J=9.0 Hz, 2H), 7.35 (d, J=9.0 Hz, 2H), 8.07 (s, 4H).

EXAMPLE 32

5-(2,4-Difluorophenoxy)-6-(4-methanesulfonylphenyl)-4-oxo-4H-pyran-2-carboxylic acid To a cooled solution of the title compound of Preparation 21 (1.50 g, 3.69 mmol) in acetone (6 ml) was added a solution of chromium (VI) oxide (0.41 g, 4.1 mmol) and sulfuric acid (3.5 ml) in water (3 ml). The mixture was stirred at 0° C. for 1 hour and at room temperature for 16 hours. The solvent was removed under reduced pressure and the residue was dissolved in ethyl acetate (50 ml). The organic solution was washed with water and with 2 N sodium hydroxide (2×50 ml). The basic phase was acidified with 2 N hydrochloric acid and extracted with ethyl acetate (2×50 ml). The combined organic extracts were washed with water (2×50 ml), dried ($Na_2SO_4$), and the solvent removed under reduced pressure. The resulting solid was recrystallized from ethanol to give 5-(2,4-difluorophenoxy)-6-(4-methanesulfonylphenyl)-4-oxo-4H-pyran-2-carboxylic acid (0.20 g, 13%) as a white solid.

m.p.: 245° C.

δ (DMSO): 3.28 (s, 3H), 6.93-6.98 (m, 1H), 7.12 (s, 1H) 7.14-7.24 (m, 1H), 7.39-7.46 (m, 1H), 8.09 (d, J=8.5 Hz, 2H), 8.14 (d, J=8.5 Hz, 2H).

EXAMPLE 33

5-(4-Chlorophenoxy)-6-(4-methanesulfonylphenyl)-4-oxo-4H-pyran-2-carboxylic acid Obtained from the title compound of Preparation 23 by the procedure described in Example 32. Recrystallization from ethyl acetate gave 5-(4-chlorophenoxy)-6-(4-methanesulfonylphenyl)-4-oxo-4H-pyran-2-carboxylic acid (25%) as an off-white solid.

m.p.: 263° C.

δ (DMSO): 3.27 (s, 3H), 7.11 (d, J=9.0 Hz, 2H), 7.12 (s, 1H), 7.35 (d, J=9.0 Hz, 2H), 8.05-8.10 (m, 4H).

EXAMPLE 34

6-(1,1-Difluoromethyl)-3-(2,4-difluorophenoxy)-2-(4-methanesulfonyl phenyl)pyran-4-one To a cooled solution of the title compound of Preparation 21 (1.0 g, 2.5 mmol) in methylene chloride (15 ml) was added (diethylamino)sulfur trifluoride (0.39 ml, 2.9 mmol). The mixture was stirred at 0° C. for 1 hour and at room temperature for 16 hours. The mixture was diluted with methylene chloride (50 ml). The organic solution was washed with water (2×50 ml), dried ($Na_2SO_4$), and the solvent removed under reduced pressure. The resulting residue was purified by column chromatography with silica gel and ethyl acetate/n-hexane (2:3) as eluent. 6-(1,1-Difluoromethyl)-3-(2,4-difluorophenoxy)-2-(4-methanesulfonylphenyl)pyran-4-one (0.20 g, 18%) as an off-white solid.

m.p.: 156° C.

δ (DMSO): 3.28 (s, 3H), 6.93-6.99 (m, 1H), 7.00 (s, 1H), 7.12 (t, $J_{F-H}$=54 Hz, 1H), 7.22-7.30 (m, 1H), 7.38-7.46 (m, 1H), 8.07 (d, J=9.0 Hz, 2H), 8.12 (d, J=9.0 Hz, 2H).

EXAMPLE 35

6-(1,1-Difluoromethyl)-3-(4-bromophenoxy)-2-(4-methanesulfonylphenyl) pyran-4-one Obtained from the title compound of Preparation 24 by the procedure described in Example 34. Purification by column chromatography with silica gel and ethyl acetate/n-hexane (1:1) as eluent gave 6-(1,1-difluoromethyl)-3-(4-bromophenoxy)-2-(4-methanesulfonylphenyl)pyran-4-one (0.58, 48%) as an off-white solid.

LRMS: m/z 471 (M+1)$^+$.

δ ($CDCl_3$): 3.08 (s, 3H), 6.53 (t, $J_{F-H}$=78 Hz, 1H), 6.85 (d, J=9.0 Hz, 2H), 7.40 (d, J=9.0 Hz, 2H), 8.00-8.11 (m, 4H).

EXAMPLE 36

6-(1,1-Difluoromethyl)-2-(4-methanesulfonylphenyl)-3-(4-methyl phenoxy)pyran-4-one Obtained from the title compound of Example 35 by the procedure described in Example 10. Purification by column chromatography with silica gel and ethyl acetate/n-hexane (2:3) as eluent gave 6-(1,1-difluoromethyl)-2-(4-methanesulfonylphenyl)-3-(4-methylphenoxy)pyran-4-one (0.20 g, 18) as an off-white solid.

m.p.: 160° C.

δ (DMSO): 2.23 (s, 3H), 3.26 (s, 3H), 6.93 (d, J=9.0 Hz, 2H) 6.98 (s, 1H), 7.09 (d, J=9.0 Hz, 2H), 7.11 (t, $J_{F-H}$=54 Hz, 1H), 8.04-8.11 (m, 4H).

EXAMPLE 37

3-Bromo-2-(1,1-difluoromethyl)-5-(2,4-difluorophenoxy)-6-(4-methanesulfonylphenyl)pyran-4-one Obtained from the title compound of Example 34 by the procedure described in Example 17. Purification by column chromatography with silica gel and ethyl acetate/n-hexane (1:2) as eluent gave 3-bromo-2-(1,1-difluoromethyl)-5-(2,4-difluorophenoxy)-6-(4-methanesulfonyl phenyl)pyran-4-one (13%) as an off-white solid.

LRMS: m/z 507 (M+1)$^+$.

δ (DMSO): 3.13 (s, 3H), 6.71-7.13 (m, 4H), 8.11 (d, J=9.0 Hz, 2H), 8.25 (d, J=9.0 Hz, 2H).

EXAMPLE 38

2-(1,1-Difluoromethyl)-5-(2,4-difluorophenoxy)-6-(4-methanesulfonyl phenyl)-3-methylpyran-4-one Obtained from the title compound of Example 37 by the procedure described in Example 19. Recrystallization from ethanol gave 2-(1,1-difluoromethyl)-5-(2,4-difluorophenoxy)-6-(4-methanesulfonylphenyl)-3-methylpyran-4-one (86%) as an off-white solid.

m.p.: 187.8-188.6° C.

δ ($CDCl_3$): 2.14 (s, 3H), 3.09 (s, 3H), 6.56-6.93 (m, 4H), 8.07 (d, J=8.7 Hz, 2H), 8.19 (d, J=8.7 Hz, 2H).

Examples 39 and 40 illustrate pharmaceutical compositions according to the present invention and procedure for their preparation.

EXAMPLE 39

Capsules 25,000 capsules each containing 100 mg of 3-(4-fluoro-2-methylphenoxy)-2-(4-methanesulfonylphenyl)-6-methylpyran-4-one (active ingredient) were prepared according to the following formulation:

| | | |
|---|---|---|
| | Active ingredient | 2.5 Kg |
| | Lactose monohydrate | 5 Kg |
| | Colloidal silicone dioxide | 0.05 Kg |
| | Corn starch | 0.5 Kg |
| | Magnesium stearate | 0.1 Kg |

Procedure

The above ingredients were sieved through a 60 mesh sieve, and were loaded into a suitable mixer and filled into 25,000 gelatine capsules.

EXAMPLE 40

Tablets 100,000 Tablets each containing 50 mg of 3-(2,4-difluorophenoxy)-6-hydroxymethyl-2-(4-methanesulfonylphenyl) pyran-4-one (active ingredient) were prepared from the following formulation:

| | | |
|---|---|---|
| | Active ingredient | 5 Kg |
| | Spray dried lactose | 19.9 Kg |
| | Microcrystalline cellulose | 3.9 Kg |
| | Sodium stearyl fumarate | 0.2 Kg |
| | Colloidal silicon dioxide | 0.2 Kg |
| | Carboxymethyl starch | 0.8 Kg |

Procedure

All the powders were passed through a screen with an aperture of 0.6 mm, then mixed in a suitable mixer for 20 minutes and compressed into 300 mg tablets using 9 mm disc and flat bevelled punches. The disintegration time of the tablets was about 3 minutes.

The invention claimed is:
1. A compound of formula (I):

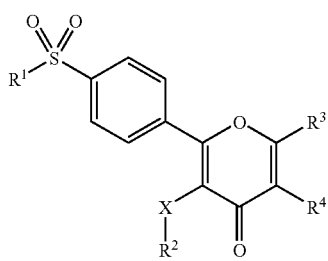

wherein:
$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkyl, hydroxymethyl, alkoxymethyl, alkenyloxymethyl, $C_3$-$C_7$ cycloalkoxymethyl, $C_3$-$C_7$ cycloalkylmethoxymethyl, benzyloxymethyl, hydroxycarbonyl, nitrile, trifluoromethyl or difluoromethyl group or a $R^7$—COO—$CH_2$— group wherein $R^7$ represents an alkyl or phenyl group;

$R^4$ represents an alkyl, alkenyl or alkynyl group or a halogen atom; and

X represents a single bond, an oxygen atom, a sulfur atom or a methylene group;

or a pharmaceutically acceptable salt thereof.

2. A compound of formula (I):

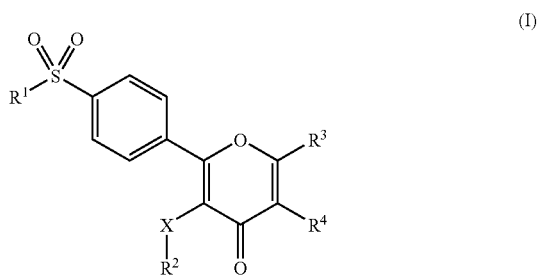

wherein:
$R^1$ represents an alkyl or —$NR^5R^6$ group, wherein $R^5$ and $R^6$ each independently represent a hydrogen atom or an alkyl group;

$R^2$ represents an alkyl, $C_3$-$C_7$ cycloalkyl, pyridyl, thienyl, naphthyl, tetrahydronaphthyl or indanyl group, or a phenyl group which may be unsubstituted or substituted by one or more halogen atoms or alkyl, trifluoromethyl, hydroxy, alkoxy, methylthio, amino, mono- or dialkylamino, hydroxyalkyl or hydroxycarbonyl groups;

$R^3$ represents an alkenyloxymethyl or $C_3$-$C_7$ cycloalkylmethoxymethyl group or a $R^7$—COO—$CH_2$— group wherein $R^7$ represents an alkyl or phenyl group;

$R^4$ represents a hydrogen atom; and

X represents a single bond, an oxygen atom, a sulfur atom or a methylene group;

or a pharmaceutically acceptable salt thereof.

3. A compound according to claim 1, wherein $R^3$ represents an unsubstituted $C_{1-3}$ alkyl, hydroxymethyl, methoxymethyl, ethoxymethyl, propoxymethyl, isopropoxymethyl, difluoromethyl, propenyloxymethyl, hydroxycarbonyl, cyclopropoxy methyl, cyclobutoxymethyl, cyclopropylmethoxymethyl, cyclobutyl methoxymethyl, nitrile or $CH_3$—COO—$CH_2$— group.

4. A compound according to claim 1, wherein $R^4$ is a chlorine or bromine atom or a methyl, ethyl, ethenyl or ethynyl group.

5. A process for producing a compound of formula (I) as defined in claim 1 which process comprises:
(a) where $R^1$ is an alkyl or —$NR^5R^6$ group in which $R^5$ and $R^6$ are alkyl groups, $R^4$ is an alkyl group, $R^3$ is an alkyl group of formula $CH_2$—$R^4$ and $R^2$ and X are as defined in claim 1, (ai) reacting a carbonyl derivative of formula (III)

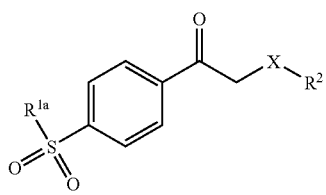
(III)

with an excess of an anhydride of formula (IX):

(R$^{4a}$CH$_2$CO)$_2$O    (IX)

or a carboxylic acid of formula (X):

R$^{4a}$CH$_2$COOH    (X)

and polyphosphoric acid at a temperature from 90° C. to 150° C.; or (aii) reacting a vinyl derivative of formula (XI):

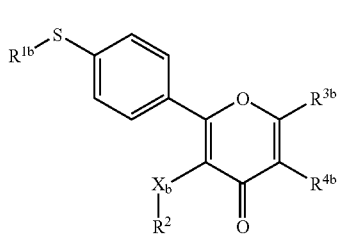
(XI)

wherein R$^{1a}$, R$^2$, R$^4$ and X are as defined above with an excess of an anhydride of formula (IX) and polyphosphoric acid at a temperature from 90° C. to 150° C.; or (b) where R$^1$ is an alkyl group, R$^3$ is an alkyl group, R$^4$ is an alkyl group, and X is as defined in claim 1 with the proviso that it is other than a sulfur atom and R$^2$ is as defined in claim 1, by reacting a mercapto derivative of formula (XIII):

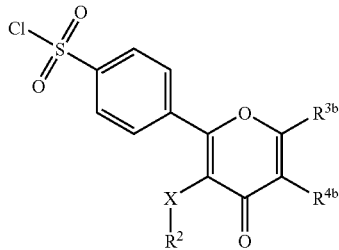
(XIII)

wherein R$^{1b}$ is an alkyl group, R$^{3b}$ is a methyl group or a R$^{4b}$CH$_2$ group, R$^{4b}$ is an alkyl group X$^b$ is as defined for X in claim 1 with the proviso that it is other than a sulfur atom and R$^2$ is as defined above, with an oxidising agent; or (c) where R$^1$ is a —NR$^5$R$^6$ group, R$^3$ is an alkyl group, R$^4$ is an alkyl group, R$^2$, R$^5$, R$^6$ and X are as defined in claim 1 by reacting a chlorosulfonyl derivative of formula (XV):

(XV)

wherein R$^2$, R$^{3b}$, R$^{4b}$ and X are as defined above with an amine of formula (XVI):

R$^5$—NH—R$^6$    (XVI)

wherein R$^5$ and R$^6$ are as defined above; or (d) where R$^1$ is a —NR$^5$R$^6$ group wherein R$^5$ and R$^6$ are hydrogen, R$^3$ is an alkyl group and R$^4$ is an alkyl group, by debenzylation of the corresponding N,N-dibenzyl derivative of formula (XIX):

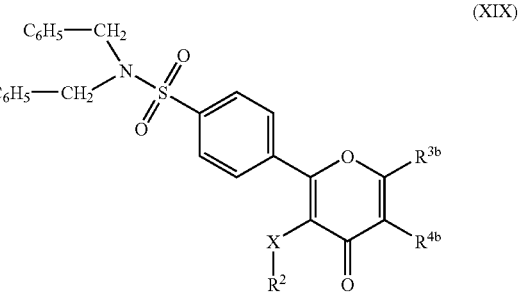
(XIX)

wherein R$^2$, R$^{3b}$, R$^{4b}$ and X are as defined; or (e) reacting a compound of formula (XXXIII):

(XXXIII)

wherein R$^{4d}$ is a chlorine, bromine or iodine atom, preferably a bromine atom and R$^1$, R$^2$, R$^3$ and X are as defined in claim 1, with a tin derivative of formula (XXXIV):

R$^{4c}$Sn(R$^9$)$_3$    (XXXIV)

wherein R$^{4c}$ is an alkyl, alkenyl or alkynyl group and R$^9$ is an alkyl group.

6. A compound according to claim 1 wherein R$^1$ represents an unsubstituted alkyl group or NH$_2$.

7. A compound according to claim 2 wherein R$^1$ represents an unsubstituted alkyl group or NH$_2$.

8. A compound according to claim 1 wherein R$^1$ is a methyl group.

9. A compound according to claim 2 wherein R$^1$ is a methyl group.

10. A compound according to claim 1 wherein X represents an oxygen atom.

11. A compound according to claim 2 wherein X represents an oxygen atom.

12. A compound according to claim 1 wherein R$^2$ is a branched alkyl, C$_3$-C$_7$ cycloalkyl, naphthyl, tetrahydronaphthyl or indanyl group, an unsubstituted phenyl group or a phenyl group substituted by one or more halogen atoms, alkyl groups and/or alkoxy groups.

13. A compound according to claim 2 wherein R$^2$ is a branched alkyl, C$_3$-C$_7$ cycloalkyl, naphthyl, tetrahydronaphthyl or indanyl group, an unsubstituted phenyl group or a phenyl group substituted by one or more halogen atoms, alkyl groups and/or alkoxy groups.

14. A compound according to claim 1 wherein $R^2$ is an unsubstituted phenyl group or a phenyl group substituted by 1, 2 or 3 substituents independently selected from chlorine, bromine, fluorine or methyl groups.

15. A compound according to claim 2 wherein $R^2$ is an unsubstituted phenyl group or a phenyl group substituted by 1, 2 or 3 substituents independently selected from chlorine, bromine, fluorine or methyl groups.

16. A compound according to claim 1 wherein $R^2$ represents a phenyl group substituted by 1 or 2 substituents independently selected from chlorine, bromine, fluorine and methyl groups.

17. A compound according to claim 2 wherein $R^2$ represents a phenyl group substituted by 1 or 2 substituents independently selected from chlorine, bromine, fluorine and methyl groups.

18. A compound according to claim 1 which is:
3-(2,4-difluorophenoxy)-6-ethyl-2-(4-methanesulfonylphenyl)-5-methyl pyran-4-one;
3-chloro-5-(2,4-difluorophenoxy)-6-(4-methanesulfonylphenyl)-2-methyl pyran-4-one;
3-chloro-5-(4-fluorophenoxy)-6-(4-methanesulfonylphenyl)-2-methyl pyran-4-one;
3-chloro-5-(4-chlorophenoxy)-6-(4-methanesulfonylphenyl)-2-methyl pyran-4-one;
3-bromo-5-(2,4-difluorophenoxy)-6-(4-methanesulfonylphenyl)-2-methyl pyran-4-one;
3-bromo-5-(4-chlorophenoxy)-6-(4-methanesulfonylphenyl)-2-methylpyran-4-one;
3-(2,4-difluorophenoxy)-5,6-dimethyl-2-(4-methanesulfonylphenyl)pyran-4-one;
3-(2,4-difluorophenoxy)-2-(4-methanesulfonylphenyl)-6-methyl-5-vinyl pyran-4-one;
3-(2,4-difluorophenoxy)-5-ethyl-2-(4-methanesulfonylphenyl)-6-methyl pyran-4-one;
3-bromo-2-(1,1-difluoromethyl)-5-(2,4-difluorophenoxy)-6-(4-methane sulfonylphenyl)pyran-4-one;
2-(1,1-difluoromethyl)-5-(2,4-difluorophenoxy)-6-(4-methanesulfonyl phenyl)-3-methylpyran-4-one;
acetic acid [5-(2,4-difluorophenoxy)-6-(4-methanesulfonylphenyl)-4-oxo-4H-pyran-2-yl]methyl ester;
acetic acid [5-(4-fluorophenoxy)-6-(4-methanesulfonylphenyl)-4-oxo-4H-pyran-2-yl]methyl ester;
acetic acid [5-(4-chlorophenoxy)-6-(4-methanesulfonylphenyl)-4-oxo-4H-pyran-2-yl]methyl ester;
or a pharmaceutically acceptable salt thereof.

19. A compound according to claim 2 which is:
3-(2,4-difluorophenoxy)-6-ethyl-2-(4-methanesulfonylphenyl)-5-methyl pyran-4-one;
3-chloro-5-(2,4-difluorophenoxy)-6-(4-methanesulfonylphenyl)-2-methyl pyran-4-one;
3-chloro-5-(4-fluorophenoxy)-6-(4-methanesulfonylphenyl)-2-methyl pyran-4-one;
3-chloro-5-(4-chlorophenoxy)-6-(4-methanesulfonylphenyl)-2-methyl pyran-4-one;
3-bromo-5-(2,4-difluorophenoxy)-6-(4-methanesulfonylphenyl)-2-methyl pyran-4-one;
3-bromo-5-(4-chlorophenoxy)-6-(4-methanesulfonylphenyl)-2-methylpyran-4-one;
3-(2,4-difluorophenoxy)-5,6-dimethyl-2-(4-methanesulfonylphenyl)pyran-4-one;
3-(2,4-difluorophenoxy)-2-(4-methanesulfonylphenyl)-6-methyl-5-vinyl pyran-4-one;
3-(2,4-difluorophenoxy)-5-ethyl-2-(4-methanesulfonylphenyl)-6-methyl pyran-4-one;
3-bromo-2-(1,1-difluoromethyl)-5-(2,4-difluorophenoxy)-6-(4-methane sulfonylphenyl)pyran-4-one;
2-(1,1-difluoromethyl)-5-(2,4-difluorophenoxy)-6-(4-methanesulfonyl phenyl)-3-methylpyran-4-one;
acetic acid [5-(2,4-difluorophenoxy)-6-(4-methanesulfonylphenyl)-4-oxo-4H-pyran-2-yl]methyl ester;
acetic acid [5-(4-fluorophenoxy)-6-(4-methanesulfonylphenyl)-4-oxo-4H-pyran-2-yl]methyl ester;
acetic acid [5-(4-chlorophenoxy)-6-(4-methanesulfonylphenyl)-4-oxo-4H-pyran-2-yl]methyl ester;
or a pharmaceutically acceptable salt thereof.

20. A method for treating pain, fever or inflammation or inhibiting prostanoid-induced smooth muscle contraction which comprises administering to a human or animal subject in need of treatment an effective amount of a compound according to claim 1.

21. A method for treating pain, fever or inflammation or inhibiting prostanoid-induced smooth muscle contraction which comprises administering to a human or animal subject in need of treatment an effective amount of a compound according to claim 2.

* * * * *